US011617352B2

(12) United States Patent
Jackson, III

(10) Patent No.: US 11,617,352 B2
(45) Date of Patent: Apr. 4, 2023

(54) METHOD AND APPARATUS FOR DETECTION OF ESTRUS AND OPTIMAL TIME FOR EMBRYO TRANSFER OR ARTIFICIAL INSEMINATION IN ANIMALS

(71) Applicant: William R. Jackson, III, Kansas City, MO (US)

(72) Inventor: William R. Jackson, III, Kansas City, MO (US)

(*) Notice: Subject to any disclaimer, the term of this patent is extended or adjusted under 35 U.S.C. 154(b) by 291 days.

(21) Appl. No.: 16/254,310

(22) Filed: Jan. 22, 2019

(65) Prior Publication Data

US 2019/0223412 A1 Jul. 25, 2019

Related U.S. Application Data

(60) Provisional application No. 62/620,687, filed on Jan. 23, 2018.

(51) Int. Cl.
 *A01K 29/00* (2006.01)
 *A01K 21/00* (2006.01)
 (Continued)

(52) U.S. Cl.
 CPC ............ *A01K 29/005* (2013.01); *A01K 21/00* (2013.01); *A61B 5/002* (2013.01); *A61B 5/0004* (2013.01);
 (Continued)

(58) Field of Classification Search
 CPC .............. A01K 21/00; A01K 2227/101; A01K 29/005; A61B 2010/0019; A61B 2503/40;
 (Continued)

(56) References Cited

U.S. PATENT DOCUMENTS 3,841,082 A 10/1974 Cuevas et al.
3,844,273 A 10/1974 Polson
 (Continued)

FOREIGN PATENT DOCUMENTS

CA 2437226 A1 1/2005
CN 101977463 A 2/2011
 (Continued)

OTHER PUBLICATIONS

"MountCount Operating Instructions," DDX, Inc. Detection & Diagnostics Technologies.
 (Continued)

*Primary Examiner* — Rene T Towa
*Assistant Examiner* — Alexander H Connor
(74) *Attorney, Agent, or Firm* — Vander Velden Law Firm, LLC; Melinda Vander Velden

(57) ABSTRACT

An apparatus and methods for detection of estrus and optimal time for embryo transfer or artificial insemination in animals. An arched polycarbonate housing is attached to an animal. A circuit board is disposed within the housing. A rechargeable battery mounted on the circuit board provides power to the apparatus. A switch mounted on the circuit board is actuated when a breeding behavior occurs. A controller mounted on the circuit board detects actuations of the switch to generate data indicative of breeding behavior. A transmitter transmits data indicative of breeding behavior to a remote receiver.

20 Claims, 22 Drawing Sheets

(51) Int. Cl.
  *A61D 17/00* (2006.01)
  *A61B 5/00* (2006.01)
  *A61B 5/11* (2006.01)
  *A61B 10/00* (2006.01)
  *A61B 5/01* (2006.01)
(52) U.S. Cl.
  CPC .......... *A61B 5/0022* (2013.01); *A61B 5/1112* (2013.01); *A61B 5/4368* (2013.01); *A61B 5/6801* (2013.01); *A61B 5/721* (2013.01); *A61B 5/725* (2013.01); *A61B 5/7264* (2013.01); *A61B 5/7275* (2013.01); *A61D 17/002* (2013.01); *A61D 17/004* (2013.01); *A01K 2227/101* (2013.01); *A61B 5/01* (2013.01); *A61B 5/1118* (2013.01); *A61B 2010/0019* (2013.01); *A61B 2503/40* (2013.01); *A61B 2560/0214* (2013.01)
(58) Field of Classification Search
  CPC .......... A61B 2560/0214; A61B 5/0004; A61B 5/022; A61B 5/0022; A61B 5/01; A61B 5/1112; A61B 5/1118; A61B 5/4368; A61B 5/6801; A61B 5/721; A61B 5/725; A61B 5/7264; A61B 5/7275; A61D 17/002; A61D 17/004; G16H 50/20; G16H 50/30; Y02A 90/10
  See application file for complete search history.

(56) References Cited

U.S. PATENT DOCUMENTS

| | | |
|---|---|---|
| 4,224,949 A | 9/1980 | Scott et al. |
| 4,232,686 A | 11/1980 | Kammlade, Jr. |
| 4,247,758 A | 1/1981 | Rodrian |
| 4,411,274 A | 10/1983 | Wright |
| 4,455,610 A | 6/1984 | Rodrian |
| 4,503,808 A | 3/1985 | McAlister |
| 4,598,275 A | 7/1986 | Ross et al. |
| 4,696,258 A | 9/1987 | Magrath et al. |
| 4,784,155 A | 11/1988 | Mills |
| 4,785,563 A | 11/1988 | Friedman |
| 4,846,106 A | 7/1989 | Leonardo |
| 4,895,165 A | 1/1990 | Blair |
| 5,003,984 A | 4/1991 | Muraki et al. |
| 5,483,276 A | 1/1996 | Brooks et al. |
| 5,542,431 A | 8/1996 | Starzl et al. |
| 5,815,077 A | 9/1998 | Christiansen |
| 5,868,100 A | 2/1999 | Marsh |
| 5,881,673 A | 3/1999 | Beach et al. |
| 5,901,660 A | 5/1999 | Stein |
| 5,927,233 A | 7/1999 | Mainini et al. |
| 5,958,704 A | 9/1999 | Starzl et al. |
| 6,104,294 A | 8/2000 | Andersson et al. |
| 6,137,415 A | 10/2000 | Rast |
| 6,236,317 B1 | 5/2001 | Cohen et al. |
| 6,236,318 B1 | 5/2001 | Yang et al. |
| 6,467,430 B1 | 10/2002 | Stampe |
| 6,967,563 B2 | 11/2005 | Bormaster |
| 7,083,575 B1 | 8/2006 | Claycomb et al. |
| 7,230,535 B2 | 6/2007 | Jackson et al. |
| 7,509,770 B2 | 3/2009 | Gardner, Jr. et al. |
| 7,669,360 B2 | 3/2010 | Davidson |
| 7,705,736 B1 | 4/2010 | Kedziora |
| 8,066,179 B2 | 11/2011 | Lowe |
| 8,979,757 B2 | 3/2015 | Mottram et al. |
| 9,000,949 B2 | 4/2015 | Keller et al. |
| 9,078,416 B2 | 7/2015 | Folkers |
| 9,119,379 B1* | 9/2015 | Yancey .................. A61B 5/1118 |
| 9,489,776 B2 | 11/2016 | Keller et al. |
| 9,538,730 B1 | 1/2017 | Torres |
| 9,826,714 B2 | 11/2017 | Garrity et al. |
| 10,039,267 B1 | 8/2018 | Thiex et al. |
| 10,075,813 B1 | 9/2018 | Struhsaker et al. |
| 10,154,655 B2 | 12/2018 | Schab et al. |
| 2003/0231551 A1 | 12/2003 | Saylor et al. |
| 2005/0012623 A1* | 1/2005 | Jackson, III ......... A61D 17/002 340/573.3 |
| 2007/0015552 A1 | 1/2007 | Bolling |
| 2007/0074671 A1 | 4/2007 | Jackson et al. |
| 2007/0221140 A1 | 9/2007 | Warren et al. |
| 2008/0125670 A1 | 5/2008 | Signorini et al. |
| 2008/0154099 A1* | 6/2008 | Aspel ..................... A61B 5/002 705/2 |
| 2009/0198112 A1* | 8/2009 | Park .................. A61B 5/02438 600/301 |
| 2010/0030036 A1 | 2/2010 | Mottram et al. |
| 2011/0063133 A1 | 3/2011 | Keller et al. |
| 2012/0144723 A1 | 6/2012 | Davidson |
| 2012/0206265 A1 | 8/2012 | Solazzo et al. |
| 2013/0222141 A1 | 8/2013 | Rhee et al. |
| 2013/0271022 A1 | 10/2013 | Pan et al. |
| 2014/0015945 A1* | 1/2014 | Bench .................. A61B 5/6887 119/421 |
| 2014/0051946 A1* | 2/2014 | Arne .................. A61B 5/0006 455/414.1 |
| 2014/0230755 A1* | 8/2014 | Trenkle ................. G01C 21/367 119/859 |
| 2014/0311215 A1* | 10/2014 | Keays ..................... A61B 5/082 73/23.3 |
| 2015/0160263 A1 | 6/2015 | Howell |
| 2016/0135433 A1 | 5/2016 | Harty et al. |
| 2016/0157979 A1* | 6/2016 | Dinger .................. A01K 11/00 600/551 |
| 2017/0272842 A1* | 9/2017 | Touma ................... A63B 43/00 |
| 2017/0280687 A1* | 10/2017 | Vrabete ................ A01K 29/005 |
| 2018/0279582 A1* | 10/2018 | Yajima .................. A01K 29/005 |
| 2019/0037040 A1* | 1/2019 | Kasaragod ............ H04L 67/125 |
| 2019/0373857 A1* | 12/2019 | Leigh-Lancaster ......................... A01K 11/008 |

FOREIGN PATENT DOCUMENTS

| | | |
|---|---|---|
| GB | 2076259 A | 11/1981 |
| JP | H0739268 A | 2/1995 |
| WO | 1995032616 A1 | 12/1995 |
| WO | 2000036907 A1 | 6/2000 |
| WO | 2000060979 A1 | 10/2000 |
| WO | 20070119070 A1 | 10/2007 |
| WO | 2015160263 A1 | 10/2015 |
| WO | 2018109725 A1 | 6/2018 |

OTHER PUBLICATIONS

Boyd, Hindsight and Foresight, Proceedings of the 14th Technical Conference on Artificial Insemination & Reproduction, 1992, pp. 6-11, vol. A1.

Brown et al., Fathead minnows avoid conspedfic and heterospedfic alarm pheromones in the faeces of northern pike, Journal of Fish Biology, Sep. 1995, pp. 387-393, vol. 47 issue 3, Wiley.

Carthew et al., Monitoring animal activity with automated photography, Wildlife Management, Oct. 1991, pp. 689-692, vol. 55 No. 4, Wiley.

Dagorn et al., Behavior of yellowfin (*Thunnus albacares*) and bigeye (*T. obesus*) tuna in a network of fish aggregating devices (FADs), Marine Biology, Mar. 30, 2006, pp. 595-606, vol. 151, Springer-Verlag.

Great Plains Livestock Technologies. Printed Jan. 31, 2019. http://greatplainslivestock.tripod.com/products.html. 2 pages.

Hoffman, The control of distress vocalization by an imprinted stimulus, Behaviour, Jan. 1, 1967, vol. 30 issue 2-3.

Huffine et al., Artificial Insemination Handbook, 1998, National Association of Animal Breeders.

IMV International Corporation. Printed Dec. 15, 2003, www.imvusa.com/Show%Heat/Showheatintro.htm. 1 page.

Schaefer et al., Movements, behavior, and habitat selection of bigeye tuna (*Thunnus obesus*) in the eastern equatorial Pacific, ascertained through archival lags, Fishery Bulletin, May 24, 2002, pp. 765-788, vol. 100(4).

(56) References Cited

OTHER PUBLICATIONS

Voegeli et al., Ultrasonic telemetry, tracking and automated monitoring technology for sharks, Environmental Biology of Fishes, Feb. 2001, pp. 267-281, vol. 60, Kluwer Academic Publishers, Netherlands.

Wagner et al., Abstracts, 14th International Congress on Animal Reproduction, Jul. 2-6, 2000, pp. 76-77, vol. 2, Stockholm.

Wiens et al., Metronome timing in behavioral ecology studies, Ecology, Mar. 1, 1970, pp. 350-352, vol. 51 issue 2, Ecological Society of America, U.S.

Willis et al., A baited underwater video system for the determination of relative density of carnivorous reef fish, Marine Freshwater Research, 2000, pp. 755-763, vol. 51, CSIRO Publishing, Australia.

\* cited by examiner

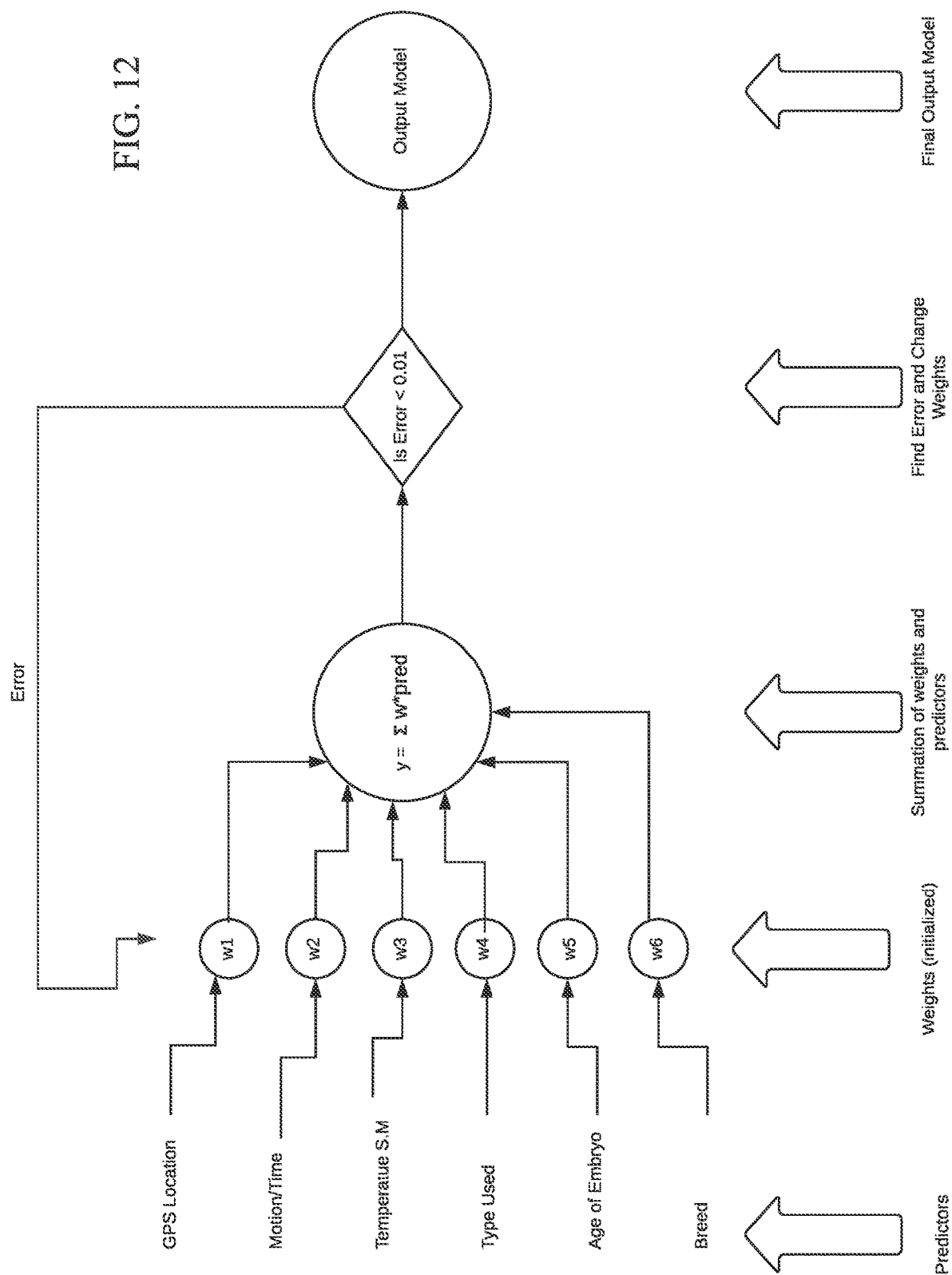

METHOD AND APPARATUS FOR DETECTION OF ESTRUS AND OPTIMAL TIME FOR EMBRYO TRANSFER OR ARTIFICIAL INSEMINATION IN ANIMALS

CROSS-REFERENCE TO RELATED APPLICATIONS

This application claims priority to U.S. Provisional Patent Application No. 62/620,687, filed on Jan. 23, 2018, the entirety of which is hereby incorporated herein by reference.

U.S. Pat. No. 7,230,535, filed on Jun. 30, 2004, is incorporated by reference for all that it contains.

FIELD OF THE INVENTION

This invention relates to the fields of electronics devices and computer programming. More particularly, it relates to an electronic estrus detection device that transmits data based on external stimuli.

BACKGROUND

In order to determine the best time to artificially inseminate or to conduct embryo transfer for animals such as cows, the time the animal is or has been in estrus must be known. Practitioners vary in their opinions as to the optimal time from estrus to artificial insemination or embryo transfer. Therefore, a method and apparatus (hereinafter the apparatus is referred to as the "end device") for providing that information should provide raw data on which different predictive models can be based that will take into account the varying conditions under which the attempt to achieve impregnation of the animal is made.

A cow standing to be mounted is the most accurate sign of estrus in cows. Other signs of estrus may include increased restlessness and motion and temperature of the animal. External conditions of the environment such as geographic location, outside temperature, age of the embryo, the type or condition of the semen used, and feeding and nutritional status of the animal can also affect the success or failure of the breeding effort.

Some prior art systems that monitored breeding were stand-alone systems, providing only visual indications to viewers. Though useful, these visual indications can be difficult to see in direct sunlight and required the viewer to be in the proximity of the device.

Other prior art systems have used radio communications to monitor standing mounts, but the devices were unable to reliably maintain adhesion to the animal.

Other prior art systems monitored the motion of the animal, temperature or other conditions, but were not designed to include a direct and reliable determination of the existence and duration of a standing mount, the most reliable indicator of estrus. For example, U.S. Pat. No. 9,826,714 to Garrity, U.S. Pat. No. 10,039,267 to Thiex, et al., U.S. patent application 20080125670 of Signorini and U.S. Patent Application 2016/0135433 of Dairymaster.

Other prior art systems did not include an extremely resilient radio transmission such as LoRa radio using the LoRaWAN protocol and were not able to be received over relatively long distances, even in terrain with obstacles blocking direct line of sight, such as trees, buildings or other objects. For example. U.S. Patent Application 2016/0157979 of Farmshed Labs Limited, U.S. Pat. No. 9,538,730 to Torres and U.S. Pat. No. 8,066,179 to Lowe.

Other prior art systems did not provide such a transmission capability with extremely low power consumption permitting the use of small batteries, retention of narrow and low device profile on the animal, and very long periods of operation without recharging.

Other prior art systems did not provide a case that has been demonstrated to be able to withstand the extreme pressure, shock, torque and humidity associated with monitoring standing mounts.

Other prior art devices were not rechargeable.

Other prior art systems did not permit the retention of data when out of the range of the receiver and the transmission of data updates when in range, so that data useful for either estrus detection or embryo transfer may be retained, even if it was obtained while the end device was outside of the range of the receiver.

Other prior art systems provided data regarding the occurrence of a standing mount but did not provide direct and reliable data regarding the existence of a standing mount and its duration, the most reliable criteria for determining estrus. For example, U.S. patent application publication 2016/0135433 of Dairymaster, U.S. Pat. No. 6,104,294 to Andersson, et al., U.S. Pat. No. 8,979,757 to Mottram, U.S. Pat. No. 9,538,730 to Torres, and U.S. Pat. No. 10,075,813 to Tioesta, LLC.

Other prior art systems did not use the LoRaWAN protocol and therefore were not able to reliably monitor very large numbers of animals on a single gateway.

Other prior art systems provide only static models of prediction of estrus such as defined thresholds not subject to increasing accuracy as additional data is accumulated. These systems are not well suited to a global system of raw data collection permitting the use of analytical systems such as machine learning that can provide superior prediction of estrus in cows and other animals under varying conditions such as breed, temperature, motion and restlessness and location.

Other prior art systems did not provide raw data regarding the existence of a standing mount and its duration in conjunction with raw data such as location, motion, and temperature and therefore, though they provide some raw data, they were not well suited to a global system of raw data collection permitting the use of analytical systems such as machine learning or deep learning employing neural nets to provide superior prediction of estrus in cows and other animals under varying conditions. For example, U.S. Pat. No. 10,154,655 xto Equus Global Holdings, LLC.

Other prior art systems did not provide the ability to combine raw data from the animal, such as the existence of a standing mount, motion, temperature and location with other data such as type of semen, age and type of embryo, outside temperature at the location, breed, feeding and nutritional status of the animal, outcome of breeding effort, or other data for use in developing better models for the prediction of estrus.

Other prior art systems were not as well suited for the monitoring of animals in less-developed areas of the world having wide ranging animals and animals that are difficult to locate or monitor due to type of terrain.

Other prior art systems were not as well-suited for the development of methods for breeding cattle and the development of breeds for use in tropical climates not presently favorable for the production of milk or the development of breeds for use in changing climatic conditions not favorable for the production of milk.

BRIEF SUMMARY

In accordance with one embodiment of the invention, an end device for detecting estrus and the optimal time for embryo transfer or artificial insemination in animals is provided. The end device has a narrow, arched and low profile so that it can be placed on the animal's tail head and be less susceptible to displacement by external forces. The end device is attached to the animal by a patch that is glued to the animal's tailhead and the area of the animal nearest to the animal's tail in a manner that assures adhesion during mounting activity or other activity of the animal and direct transduction of a standing mount. A transducer receives a stimulus, a microcontroller validates that the stimulus received was incident to a mating-behavior incident, the data regarding the time and length of the mount is stored in the microcontroller, is designated as a first, second, third, etc. mating-behavior incident, and the event is assigned a unique identifier for that mating-behavior incident. When in range of a receiver, the data is transmitted by a LoRa radio using the LoRa WAN protocol or a similar radio protocol to a receiver and is stored in a database linked to a global database for use by veterinarians, scientists, dairypersons and others. When not in range, the data is stored and is transmitted later, when the transmitter is in range of the receiver.

In accordance with another embodiment, in addition to the above, the end device stores and transmits data regarding location, motion and restlessness of the animal, and temperature. That additional information is transmitted to a receiver in the same fashion as stated in the previously described embodiment. The raw data regarding standing mounts, location, motion, and restlessness and temperature are stored in a database along with additional data that is entered into the database and is attached to linked identifiers for the animal and the end device. That additional data may include, for example, breed, geographic location, age of embryo, type of semen, outside temperature at the location, feeding and nutritional status of the animal, and success or failure of the breeding attempt. The additional data can be entered for many end devices simultaneously if it is the same for a group of devices, for example, geographic location, breed or semen type. All of the data can be used by veterinarians, scientists, dairypersons and others to determine the best indicators for the timing of attempts to conduct artificial insemination or embryo transfer.

In another embodiment, the raw data received from the end device and the other additional data entered into the database is stored and used by a computer using machine learning methods such as linear regression, K-Means clustering or neural nets to provide increasingly accurate predictions regarding the timing of artificial insemination or embryo transfer, and other factors such as the optimal age of an embryo to be used for the embryo transfer in light of all of the data available pertaining to a particular breeding attempt.

In another embodiment, data derived from the above described human analysis or machine learning is fed back to the end device by radio transmission or other means to an onboard neural net that predicts whether animal activity such as the various length and frequency of mounting activity and associated motion and restlessness of the animal that is monitored by the end device is actually caused by estrus.

Accordingly, several advantages of one or more aspects of the present invention are as follows: to provide a means for detecting animal estrus that provides a valid indication of mounting activity while remaining adhered to the animal, that provides transmission of the data without direct line of sight, that provides raw data regarding mounting activity, motion and restlessness, location and internal and external temperatures, that permits monitoring of numerous animals with a single gateway, that preserves data when transmission is not possible, and that provides a global system of data collection used for analysis and the development of superior predictive models of optimal times for insemination or embryo transfer using various means including but not limited to linear regression, K-Means clustering, neural nets, or other methods of predicting and determining the existence of estrus. The present invention provides a superior means for monitoring animals in less-developed areas of the world having wide ranging animals and animals that are difficult to locate or monitor due to type of terrain. The present invention provides a superior means for the development of methods for monitoring and breeding cattle in tropical climates not presently favorable to the production of milk and is better suited for the development of methods for breeding cattle.

BRIEF DESCRIPTION OF THE DRAWINGS

FIG. 12 shows an aspect of an embodiment of the present invention using a random forest committee of logistic regression to identify the probability of whether the animal is in estrus.

DETAILED DESCRIPTION

Figure 1A:
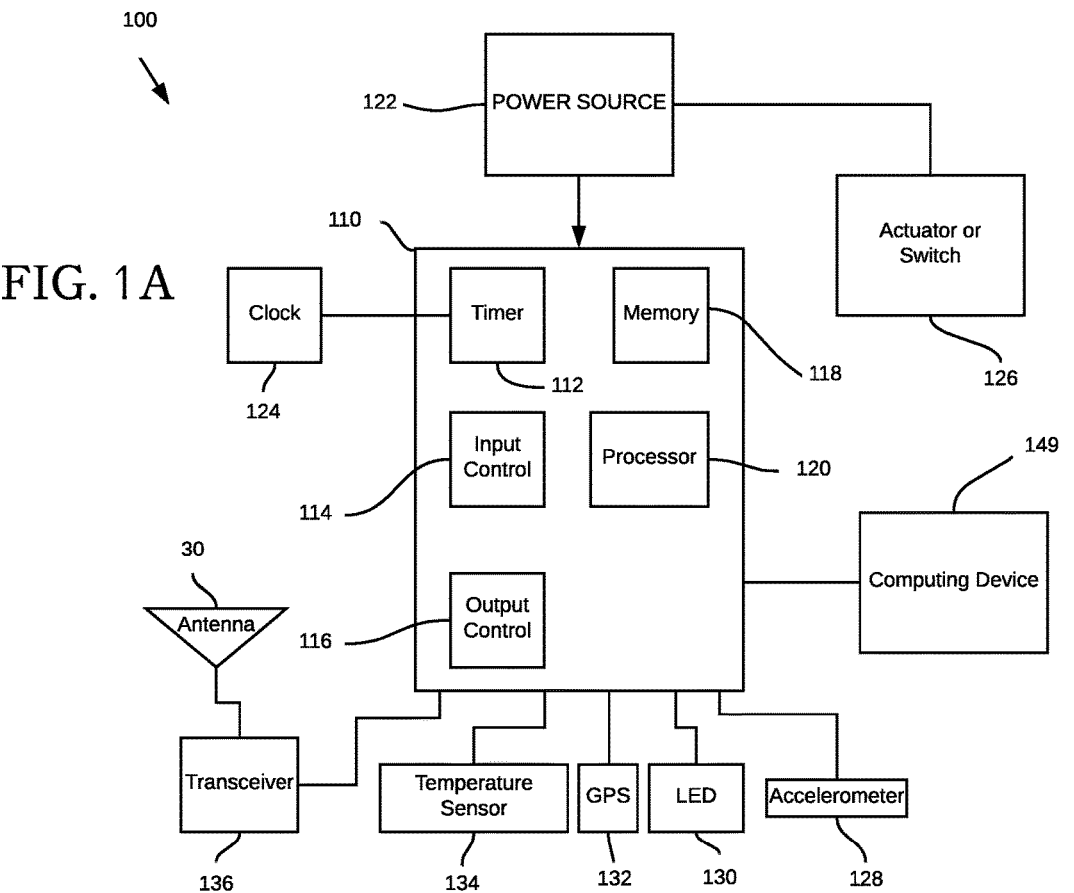
FIG. 1A shows an illustrative operating environment suitable for practicing the end device of the invention.

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. Some components of the apparatus are not shown in one or more of the figures for clarity and to facilitate explanation of embodiments of the present invention.

Some embodiments are configured to be used to monitor the breeding behavior of other domestic animals such as horses, pigs, goats, llamas, alpacas, donkeys, camels, and other bovines. As yet another example, some embodiments are configured to be used to monitor captive animals, such as those in zoos. As yet another example, some embodiments are configured to be used to monitor endangered or threatened animals. In all of these examples, these embodiments of the invention may be used to research the breeding behavior, assist the breeding process, prevent the breeding process, or some combination thereof.

The breeding monitor system may comprise more than one computing device 149 to facilitate the functions and features described herein. Computing device(s) 149 may comprise any number and combination of processors, controllers, integrated circuits, programmable logic devices, or other data and signal processing devices for carrying out the functions described herein, and may additionally comprise one or more memory storage devices, transmitters, receivers, and/or communication busses for communicating with the various devices of the breeding monitor system.

The computer program of embodiments of the invention comprises a plurality of code segments executable by the computing device(s) 149 for performing the steps of various methods of the invention. The steps of the method may be performed in the order discussed, or they may be performed in a different order, unless otherwise expressly stated. Furthermore, some steps may be performed concurrently as opposed to sequentially. Also, some steps may be optional. The computer program may also execute additional steps not described herein. The computer program, system, and method of embodiments of the invention may be implemented in hardware, software, firmware, or combinations thereof using the breeding monitor system, which broadly comprises server devices, computing devices, and a communication network.

The computer program of embodiments of the invention may be responsive to user input. As defined herein user input may be received from a variety of computing devices including but not limited to the following: desktops, laptops, calculators, telephones, smartphones, or tablets. The computing devices may receive user input from a variety of sources including but not limited to the following: keyboards, keypads, mice, trackpads, trackballs, pen-input devices, printers, scanners, facsimile, touchscreens, network transmissions, verbal/vocal commands, gestures, button presses or the like.

LoRaWAN transceiver, gateway and server140, remote server 144 and computing device(s) 149 may include any device, component, or equipment with at least one processing element and at least one memory element. The processing element may implement operating systems, and may be capable of executing the computer program, which is also generally known as instructions, commands, software code, executables, applications ("apps"), and the like. The at least one processing element may comprise processors, microprocessors, microcontrollers, field programmable gate arrays, and the like, or combinations thereof. The at least one memory element may be capable of storing or retaining the computer program and may also store data, typically binary data, including text, databases, graphics, audio, video, combinations thereof, and the like. The at least one memory element may also be known as a "computer-readable storage medium" and may include random access memory (RAM), read only memory (ROM), flash drive memory, floppy disks, hard disk drives, optical storage media such as compact discs (CDs or CDROMs), digital video disc (DVD), and the like, or combinations thereof. In addition to the at least one memory element, the server devices may further include file stores comprising a plurality of hard disk drives, network attached storage, or a separate storage network. [0026] The computing device(s) 149 may specifically include mobile communication devices (including wireless devices), work stations, desktop computers, laptop computers, palmtop computers, tablet computers, portable digital assistants (PDA), smart phones, and the like, or combinations thereof. Various embodiments of the computing device may also include voice communication devices, such as cell phones and/or smart phones. In preferred embodiments, the computing device will have an electronic display operable to display visual graphics, images, text, etc. such as visual display and means to view and enter data 148. In certain embodiments, the computer program facilitates interaction and communication through a graphical user interface (GUI) that is displayed via the electronic display. The GUI enables the user to interact with the electronic display by touching or pointing at display areas to provide information to the breeding monitor system.

The communication network may be wired or wireless and may include servers, routers, switches, wireless receivers and transmitters, and the like, as well as electrically conductive cables or optical cables. The communication network may also include local, metro, or wide area networks, as well as the Internet, or other cloud networks. Furthermore, the communication network may include cellular or mobile phone networks, as well as landline phone networks, public switched telephone networks, fiber optic networks, or the like.

The computer program may run on computing device(s) 149 or, alternatively, may run on one or more server devices such as LoRaWAN transceiver, gateway and server 140 or remote server144. In certain embodiments of the invention, the computer program may be embodied in a stand-alone computer program (i.e., an "app") downloaded on a user's computing device 149 or in a web-accessible program that is accessible by the user's computing device 149 via the communication network. As used herein, the stand-alone computer program or web-accessible program provides users with access to an electronic resource from which the users can interact with various embodiments of the invention.

In embodiments of the invention, users may be provided with different types of accounts. Each type of user account may provide their respective users with unique roles, capabilities, and permissions with respect to implementing embodiments of the invention. For instance, a caretaker may be provided with a caretaker account configured to provide access to specific animals for breeding. Additionally, a veterinarian may be provided with a medical account related to overall and specific breeding trends. In addition, any number and/or any specific types of account are provided to carry out the functions, features, and/or implementations of the invention. Upon the user logging in to the electronic resource for a first time, they may be required to provide various pieces of identification information to create their respective accounts. Such identification information may include, for instance, personal name, business name, email address, phone number, or the like. Upon providing the identification information, the user may be required to enter (or may be given) a username and password, which will be required to access the electronic resource.

Figure 1B:
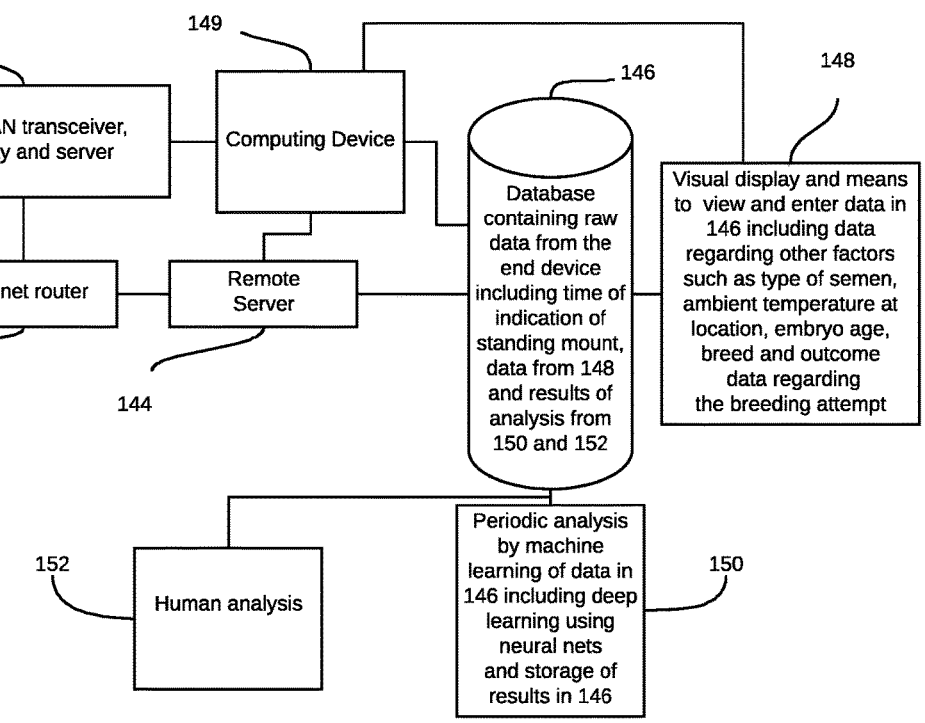
FIG. 1B shows in illustrative operating environment suitable for practicing the method for using the raw data received from the end device.

FIG. 1A and FIG. 1B illustrate a block diagram exemplary operating environment 100 suitable for practicing the present invention. Operating environment 100 is provided for illustrative purposes to describe an exemplary embodiment for performing the functionality described in the flow diagrams, which will be described in greater detail with reference to FIG. 11A-11I. Those skilled in the art will appreciate a variety of alternative operating environments that provide the functional aspects described below. FIGS. 1A and 1B are illustrative in nature and should not be construed as a limitation of the present invention.

FIG. 1A depicts an operating environment 100 for the end device 1. In one embodiment, operating environment 100 includes a controller 110, which may include a timer 112, an input-control component 114, an output-control component 116, a memory 118, and a processor 120. Timer 112 can receive an incoming clock signal and manipulate the signal to comply with desired parameters and track passage of time. Memory 118 can be, as described above, any computer-readable media for storing and reading computer-useable instructions. Memory 118 is preferably nonvolatile, so as to preserve historical data in the absence of a power source. Processor 120 coordinates data flow through the various subcomponents of controller 110, all of which are not shown due to their conventional nature. Although a litany of devices may be used, exemplary controllers 110 suitable for use in the present invention include the PIC16LF1847 or the ATSAMR34J16 Microcontrollers offered by Microchip Technology Incorporated of Chandler, Ariz.

In one embodiment, controller 110 communicates with a power source 122, an actuator or switch 126, a timing device or clock 124, a motion detecting device such as an accelerometer 128, a presentation interface such as an LED 130, a GPS receiver 132, a heat detecting device such as a temperature sensor 134 and a transceiver 136. Power source 122 includes one or more lithium polymer batteries in one embodiment but could be any device that provides power to the system, such as a solar-panel array or a kinetic device that is motion-powered. When used, the batteries are preferably maintained in place. The power source 122 is rechargeable. The end device 1 is configured so that controller 110 and transceiver 136 are ordinarily in a low current sleep mode so that low power consumption permits use of the end device 1 without recharging for many months. Transceiver 136 is a LoRa radio configured to function within the LoRaWAN protocol and is therefore able to transmit for great distances with low power. The end device 1 has been tested and shown to transmit successfully for at least one and one-half miles without direct line of sight while using very little power. In one embodiment, antenna 30 is a helical antenna that has been demonstrated to provide effective transmission from the end device 1 to the LoRaWAN transceiver, gateway and server 140 when the end device 1 is in a variety of attitudes and is at a far distance.

Clock 124 provides timing functionality to controller 110. The controller 110 may record or analyze various data about the sensing of the breeding behavior, such as time, number, intensity, duration, interval, rates of change, and other information. Actuator or switch 126 can be any type of actuating device that signals the happening of a mounting-behavior event. In some embodiments, the entire casing that houses the electronics of the device can trigger actuator or switch 126 in a pressure-sensitive embodiment. Thus, the casing can act as a switch. This embodiment is useful to increase the surface area available to receive mounting-behavior stimuli. Actuator or switch 126 can be normally opened or normally closed and can be in the form of a hardware embodiment or software embodiment, such as a proximity sensor.

In one embodiment, the end device 1 can be reset by deliberate sequencing of actuator or switch 126 in a manner not likely to be caused by an animal 52. In one embodiment, flashing of presentation interface such as an LED 130 indicates to an observer that the device is being reset. In other embodiments, flashing of presentation interface such as an LED 130 may also provide periodic visual mounting behavior feedback to an observer as a supplement to the data received through the radio transmission.

FIG. 1B depicts a suitable operating environment for receiving and using the raw data transmitted from the end device 1. LoRaWAN transceiver, gateway and server 140 receives the radio transmission from the end device 1 shown in FIG. 1A. Various devices may be used as LoRaWAN transceiver, gateway and server 140 but the MultiConnect® Conduit™ IP67 Base Station produced by Multi-Tech Systems, Inc. of Mounds View, Minn. is exemplary.

Raw data from LoRaWAN transceiver, gateway and server 140 is routed through internet router 142 to remote server 144 and stored in database 146. Database 146 is connected directly, wirelessly or through any appropriate media to a visual display and means to view and enter data 148 regarding other factors not received from the end device 1 such as type of semen, outside temperature at the animal's 52 location, geographic location, the age of the embryo used if embryo transfer is employed, breed of the animal 52, feeding and nutritional status of the animal 52, and outcome data regarding the breeding attempt. The remote server 144 is configured to receive, the breeding indication. The breeding indications may be logged, analyzed, stored, or otherwise processed by the computing device 149 and visual display and means to view and enter data 148. The processing identifies trends for specific animals, for specific breeds of animal, for specific species of animal, for animals of a certain age, for animals in a specific geographic region, or other characteristics.

Data in database 146 undergoes periodic analysis by machine learning 150 that may include deep learning using neural nets and the results are stored in database 146. Human analysis 152 of the data in database 146 may occur separately or in conjunction with the machine learning shown at 150.

In some embodiments, the computing device 149 uploads or otherwise transfers data to a remote server144 (e.g., a cloud-based system or otherwise stored on the internet). The visual display and means to view and enter data 148 and the computing device 149 may additionally create a database 146 or send the data to database 146. This can allow the user to receive or otherwise access the information from an internet-enabled smart phone, a laptop computer stored in a vehicle of the user, or other computing device 149 and visual display and means to view and enter data 148. In some embodiments, this information may be encrypted, such that the user device must decrypt the information. Based upon the information provided, the user may then select certain animals for artificial insemination, embryo transfer, or other activities. The computing device 149 may select, recommend, highlight, determine, or otherwise indicate one or more animals for the above-mentioned activities. The present invention will accumulate large amounts of data from thousands of animals 52 in many locations on the earth for storage in database 146 and for analysis. Data will be received from many different users of the system. This will permit detection of patterns as more data accumulates and will provide more accurate predictions of estrus and the optimal time for artificial insemination or embryo transfer. Training of neural nets or other machine training will also permit the deployment of other instruments used to detect estrus based on the machine training models obtained.

Figure 2:
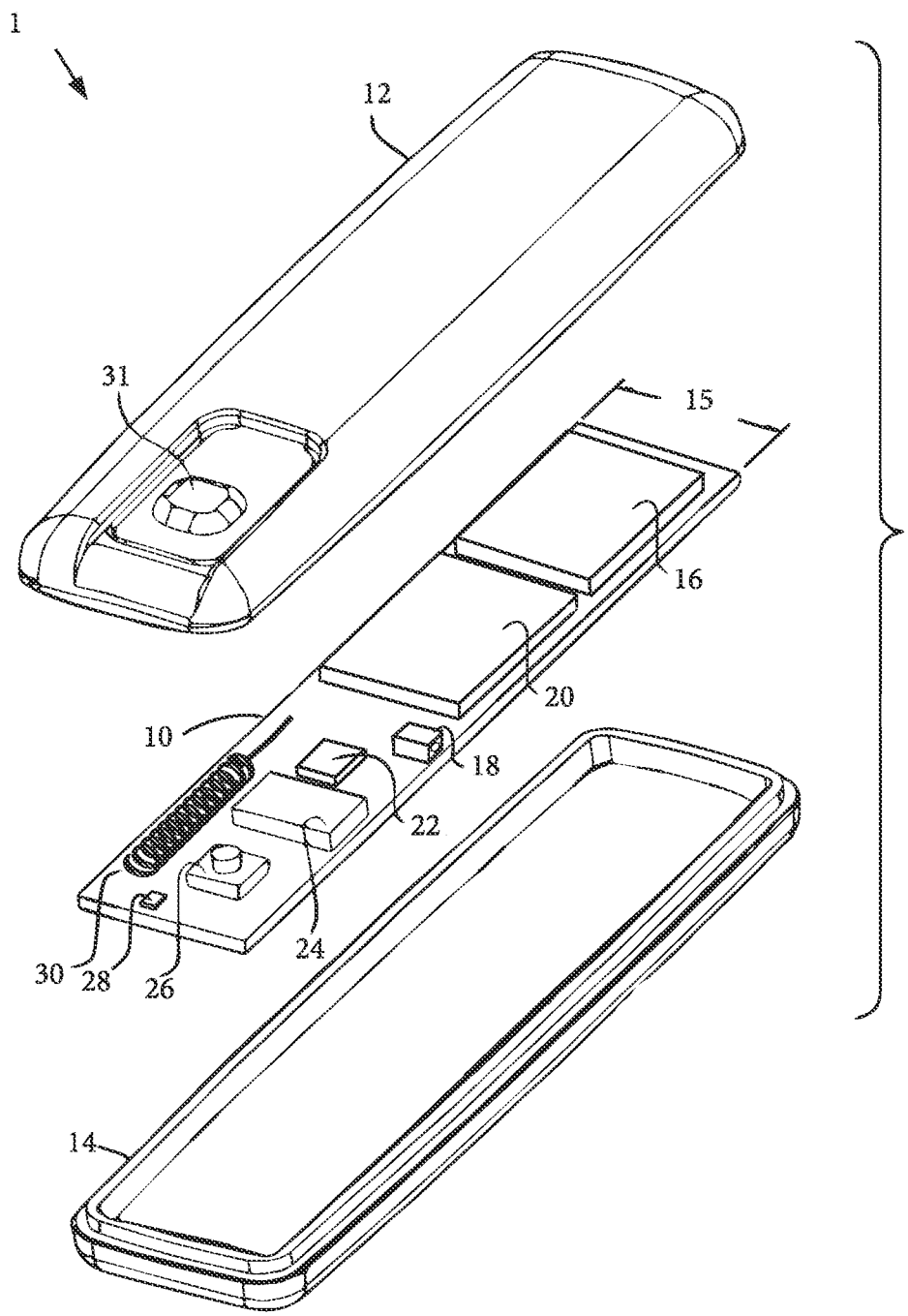
FIG. 2 shows the end device in an exploded view in accordance with one embodiment.

FIG. 2 shows an exploded view of an embodiment of the end device 1 employing LoRa radio and using the LoRaWAN protocol. Circuit board 10, top of case 12 and bottom of case 14 are designed to provide secure placement and adhesion to the animal's 52 tailhead when compared with other devices, as confirmed by testing in the field. The narrow width of the circuit board 15 together with the relatively low profile and slight curvature of the case permits adhesion and secure placement on the animal 52 without displacement during a standing mount or other animal 52 activity. Other devices designed to be placed on the tailhead to provide direct measurement of a standing mount are subject to greater torque and consequent displacement due to the height or width dimensions of those devices. End device 1 is also able to withstand extreme pressure and force exerted on it during standing mounts due to its design, including the sight curvature and arching of elements of the design of top of case 12 and bottom of case 14. Battery 16 is a battery that provides sufficient peak current for long range transmission and is rechargeable. In one embodiment, battery 16 is a lithium polymer battery. Recharging port 18 permits recharging of the battery 16. LoRaWAN radio module 20 permits long range radio communications using the LoRaWAN protocol. Due to the use of chirp spread spectrum-based modulation, the radio communication is highly resistant to in or out of band interference mechanisms. Due to the use of automatic data rates permitted by the LoRaWAN protocol, the network capacity is enhanced. The use of this protocol renders the need for multiple gateways or transmission hopping unnecessary for most applications. Thousands of animals 52 can be monitored with a single gateway at great distances without the necessity of signal hopping, even with a lack of line of sight. In some embodiments, use of the LoRaWAN protocol permits determination of the distance to the end device 1 and, in other embodiments, determination of the location of the end device 1 can be achieved using multiple gateways. An antenna 30 connected to the LoRaWAN radio module 20 boosts signals transmitted by the LoRaWAN radio module 20.

In one embodiment, crystal 22 provides oscillation and accurate timing for microcontroller 24. Microcontroller 24 is able to send UART communications to LoRoWAN radio module 20 and is able to operate using extremely low current while in a sleep mode. In one embodiment, LoRaWAN radio module 20 receives instructions from microcontroller 24 and is also able to operate using extremely low current while in a sleep mode.

Switch 26 is actuated by contact with button housing 31 when a mount occurs or when user actuated to cause a reset of the device to its initial condition. In one embodiment, user action to cause a reset of the device consists of five quick presses of switch 26. This method insures that animal 52 activity does not cause an accidental reset of the device. Switch 26 can be any type of actuating device that signals the happening of an event. In some embodiments, the entire casing that houses the electronics of the device can trigger switch 26 in a pressure-sensitive embodiment. Thus, the casing can act as a switch. This embodiment is useful to increase the surface area available to receive mounting-behavior stimuli. Switch 26 can be normally opened or normally closed and can be in the form of a hardware embodiment or software embodiment, such as a proximity sensor. A single-button embodiment makes the present invention easier to operate.

In one embodiment, LED 28 displays a series of quick flashes to indicate that the device is resetting. In other embodiments, it flashes to indicate that a transmission is occurring. In some embodiments it flashes periodically to signal the existence of a prior standing mount.

In some embodiments, antenna 30 is a helical antenna that has been shown in testing to permit very long-range transmission even when the device is in varying attitudes relative to the LoRaWAN transceiver, gateway and server 140. (Shown in FIG. 10)

Figure 3:
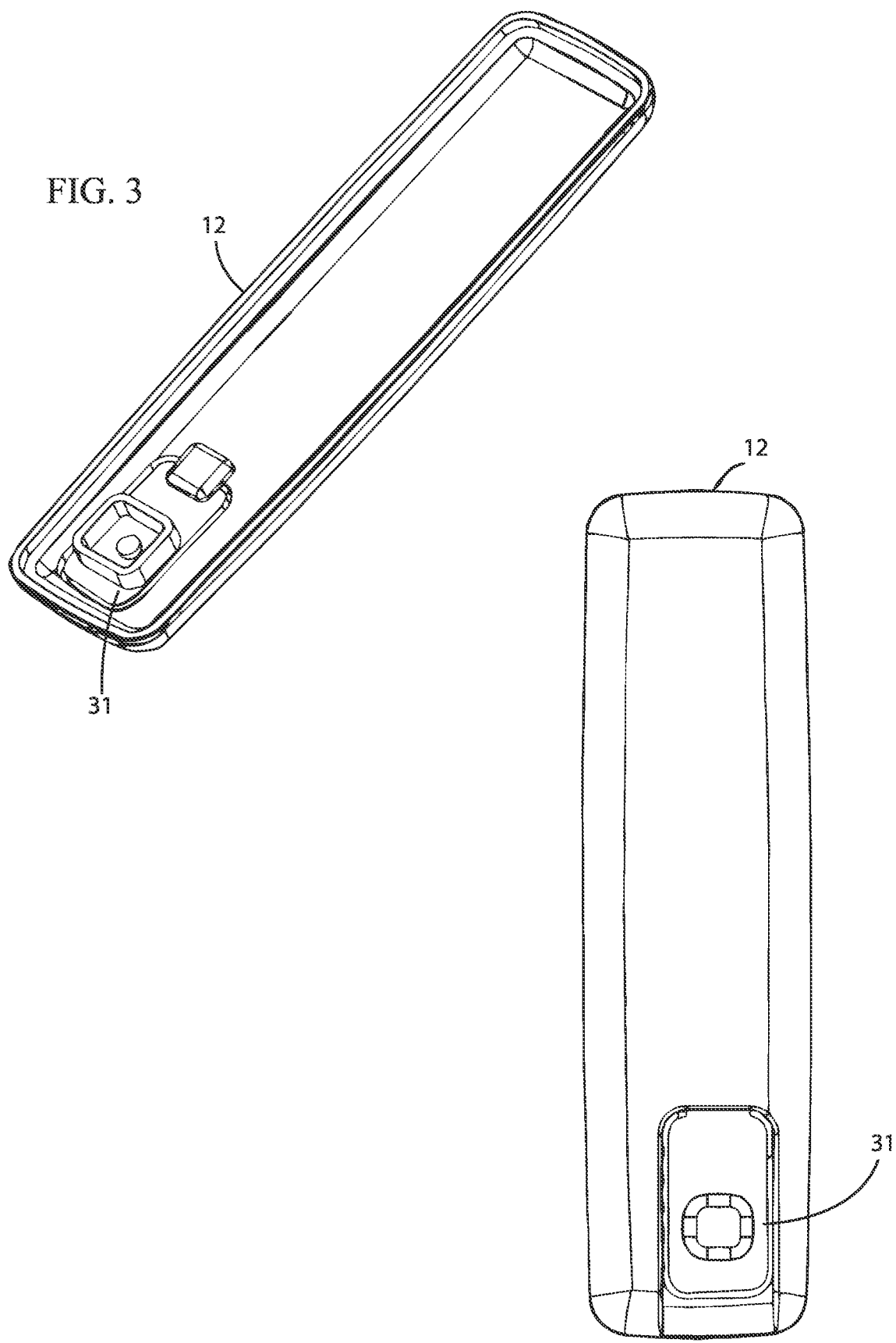
FIG. 3 shows two views of the top of the case for the end device in accordance with one embodiment.
Figure 4:
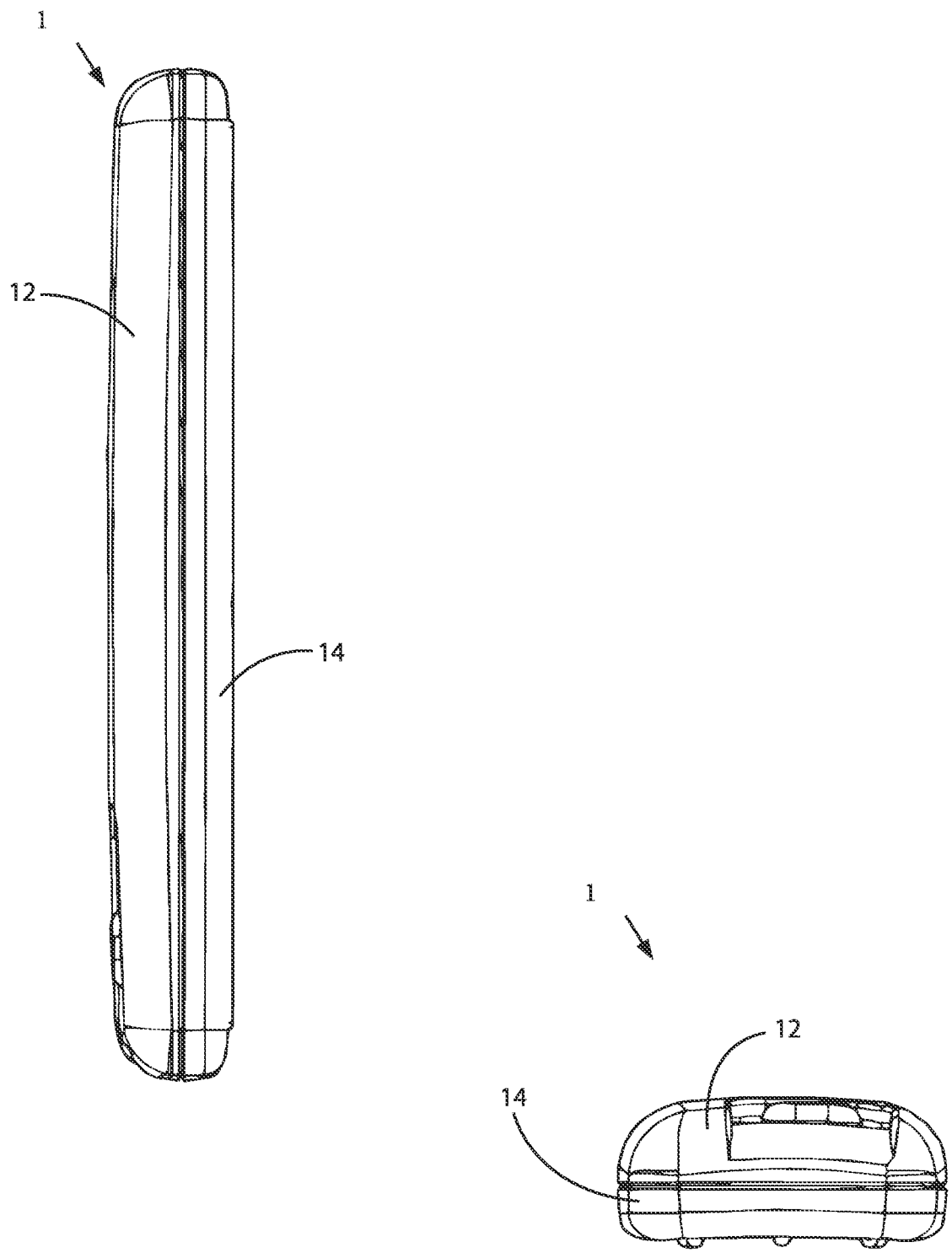
FIG. 4 shows two views of the case for the end device when the top and bottom of the case are joined, as in ordinary use and in accordance with one embodiment.
Figure 6:
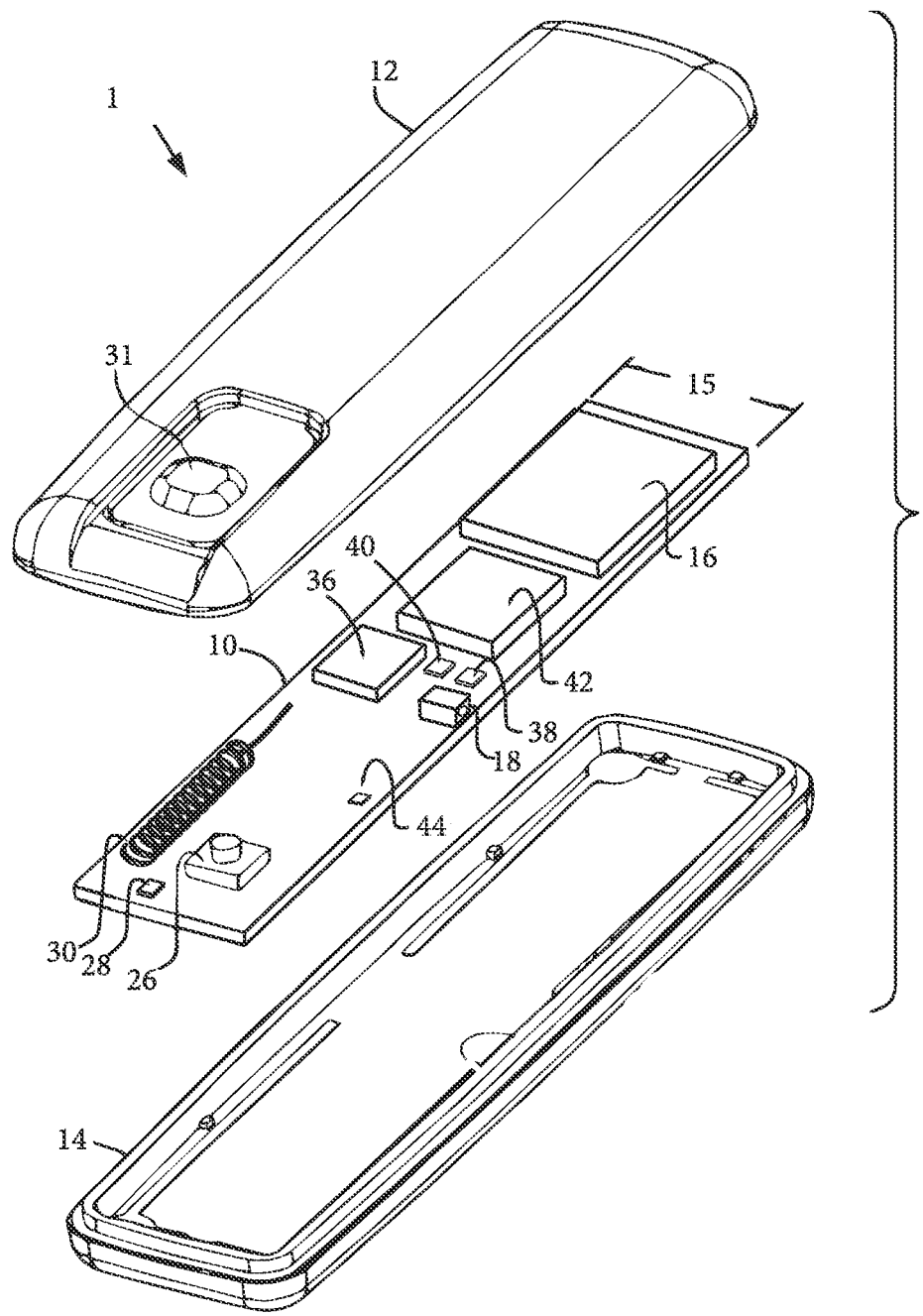
FIG. 6 shows the end device in an exploded view in accordance with another embodiment.

In FIG. 3, a bottom view and a top view of top of case 12 is shown. This case design is exemplary only and other case designs with a different button housing other than button housing 31 may be used to accommodate different actuators to provide a stimulus to the microcontroller 24 or microcontroller with a built-in LoRa radio 36 (FIG. 6). All case designs must be narrow enough not to extend beyond the width of the animal's 52 tailhead so as to avoid rocking, short enough to remain flat on the animal's 52 tailhead, and low enough to avoid excessive impact or torque from lateral forces. When assembled as shown in FIG. 4, the end device 1 should be no more than 108 mm in length, 29 mm in width and 13.7 mm in height. Testing has demonstrated that, by remaining within these constraints and by using the method of attaching the device to the animal 52 described more fully below with reference to FIGS. 7, 8, 9 and 10, the end device 1 can remain securely attached to the animal 52 during use. It should be noted that the case design is, in many respects, as substantially described in U.S. patent 20050012623 A1 published Jan. 20, 2005 to James Timothy Jackson and the present inventor. The use of this case provides an advantage to the present invention. This case design also provides an arched design that has been demonstrated to provide superior strength when undergoing extreme force and has been shown to successfully protect the device from damage during standing mounts. This and the dimensions discussed above are some of the factors rendering this device superior than the prior art for the reliable and repeated transmission of data regarding standing mounts. In some embodiments, the case is made of semi-transparent polycarbonate.

In FIG. 4 a view of top of case 12 and bottom of case 14 is shown as they appear when they are enclosing the circuit board in ordinary use. As stated above, this design is exemplary only. It should be noted that in operation on the back of an animal 52 the device is subject to extreme conditions including shock and extreme humidity. The present invention has been proven to be able to survive these conditions over long periods of time and remain operating. In some embodiments, a silicon-based substance of an appropriate viscosity and adhesion is used as a part of the present invention and is applied to the interior of the case and the circuit board. In one embodiment, the viscosity of the silicon-based substance is 2,800 cps.

Figure 5:
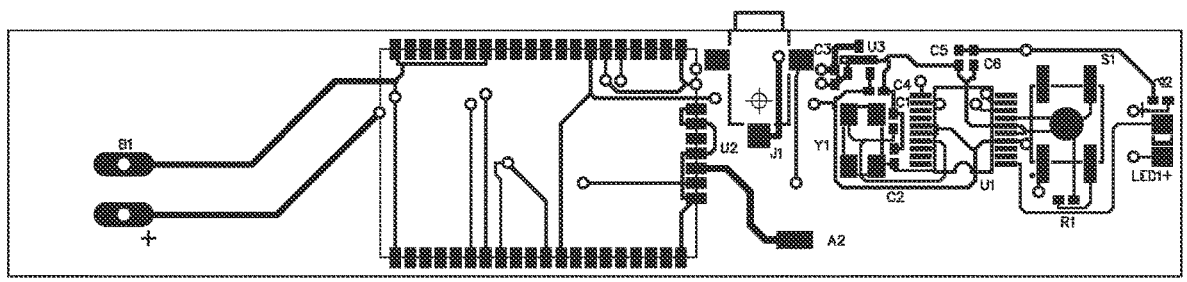
FIG. 5 shows the printed circuit board design in accordance with one embodiment.

FIG. 5 shows a printed circuit board design suitable for the embodiment shown in FIG. 2. Many other printed circuit board designs are suitable, and FIG. 5 is exemplary only.

In FIG. 6, another embodiment of the end device 1 is shown. In this embodiment, a microcontroller with a built-in LoRa radio 36 for use with the LoRaWAN protocol is used. In this embodiment, a temperature sensor 38, an accelerometer 40 and a GPS module 42, are used to provide raw data regarding those parameters. In this embodiment, a patch antenna 44 is used for the GPS module.

Figure 7:
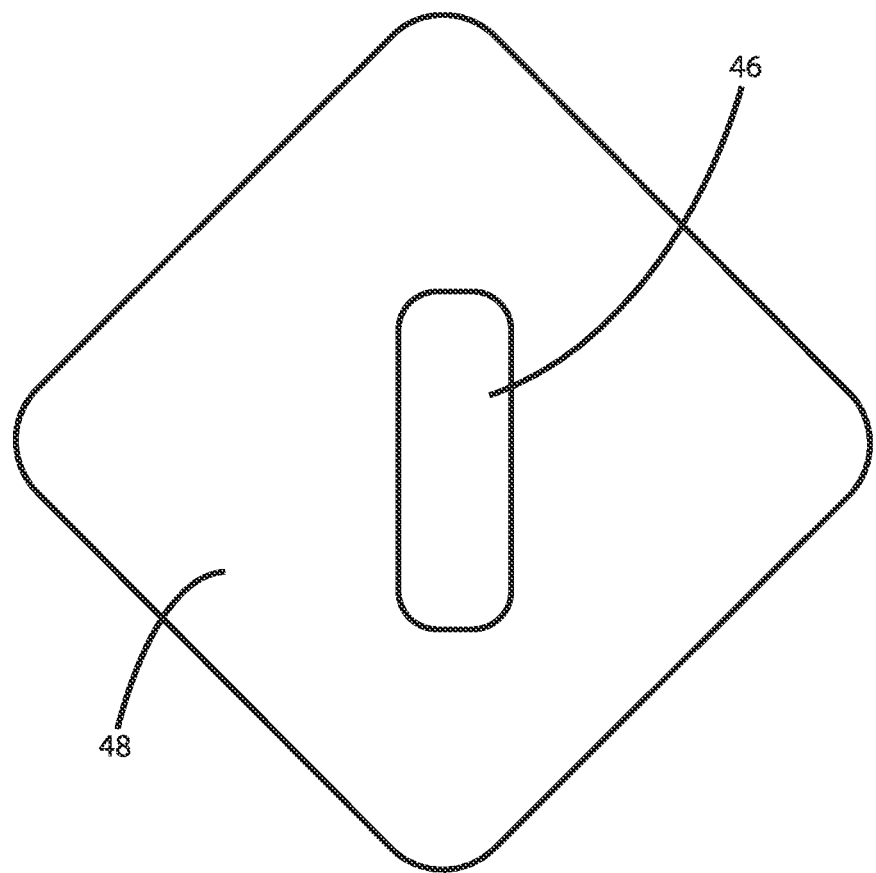
FIG. 7 show the pouch and the patch used in conjunction with an adhesive to secure the device to the area of the tailhead of the animal.

FIG. 7 shows pouch 46 used to house the end device 1 while it is in use, and the patch 48 used to attach the end device 1 to the animal 52. Pouch 46 can be made of various materials but in one embodiment it is made of clear vinyl. In another embodiment, pouch 46 is made of nylon. Patch 48 can be made of various materials, but it should be strong enough not to tear under use and sufficiently absorbent to absorb an adhesive as will be described more fully below. In one embodiment, patch 48 is made of cotton cloth. Pouch 46 is adhered to patch 48 by using heat.

Figure 8:
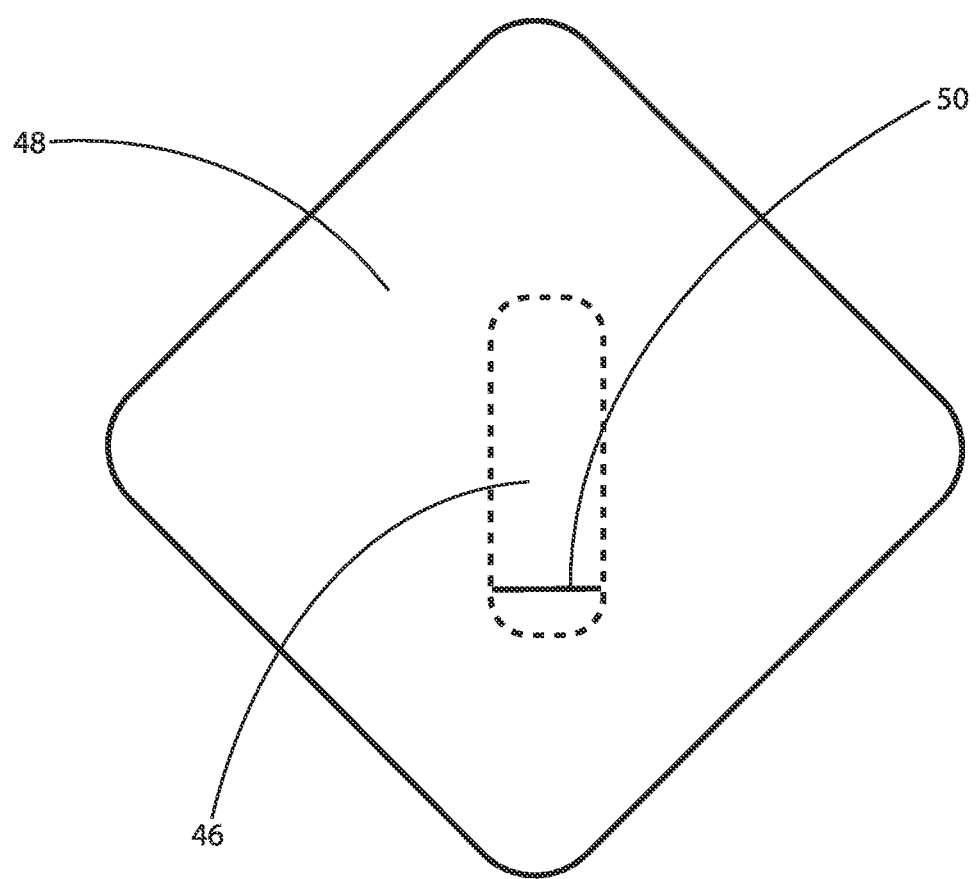
FIG. 8 shows the bottom of the patch used in conjunction with an adhesive to secure the device to the area of the tailhead of the animal and the slot used to insert the end device.

FIG. 8 shows patch 48 and slot 50. Slot 50 is positioned underneath pouch 46 and provides access to the interior of the pouch 46. The user inserts or removes the end device 1 through slot 50 as needed.

Figure 9:
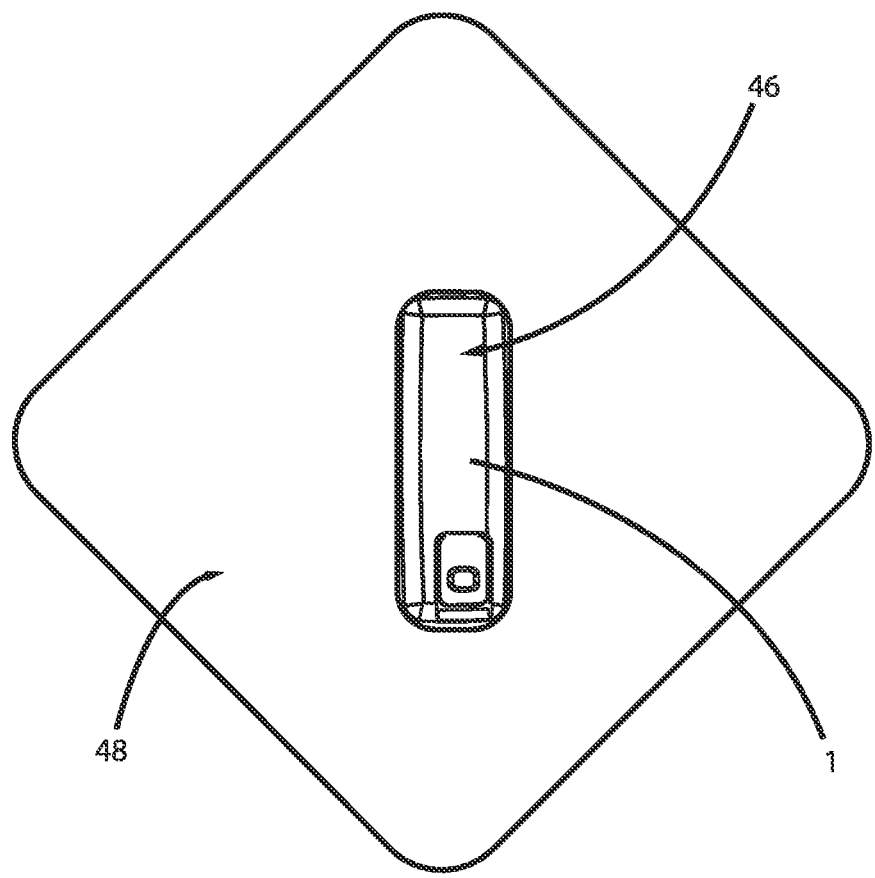
FIG. 9 shows the end device when inserted into the pouch for use.

FIG. 9 shows the patch 48 with the end device 1 inserted into pouch 46 as in normal use. The end device 1 should be oriented so that button housing 31 is nearest to the tail of the animal 52.

Figure 10:
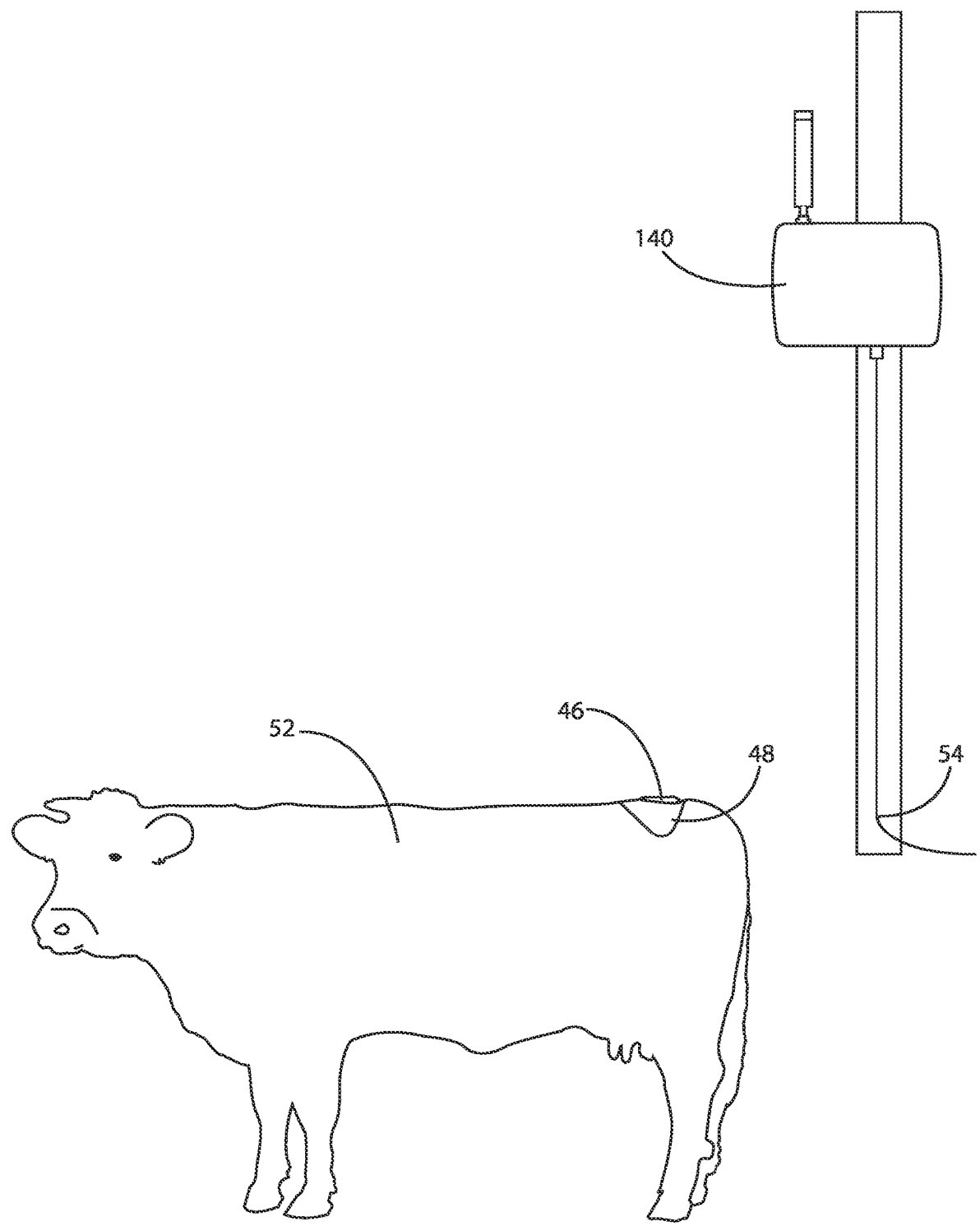
FIG. 10 shows the use of the end device while inserted in the pouch and while the patch is adhered to the area of the tailhead of the animal.

FIG. 10 shows the use of the end device 1 while inserted in the pouch 46 and while patch 48 is adhered to the area of the tailhead of the animal 52. The end device 1 should be oriented so that button housing 31 is nearest to the tail of the animal 52.

Figure 11A:
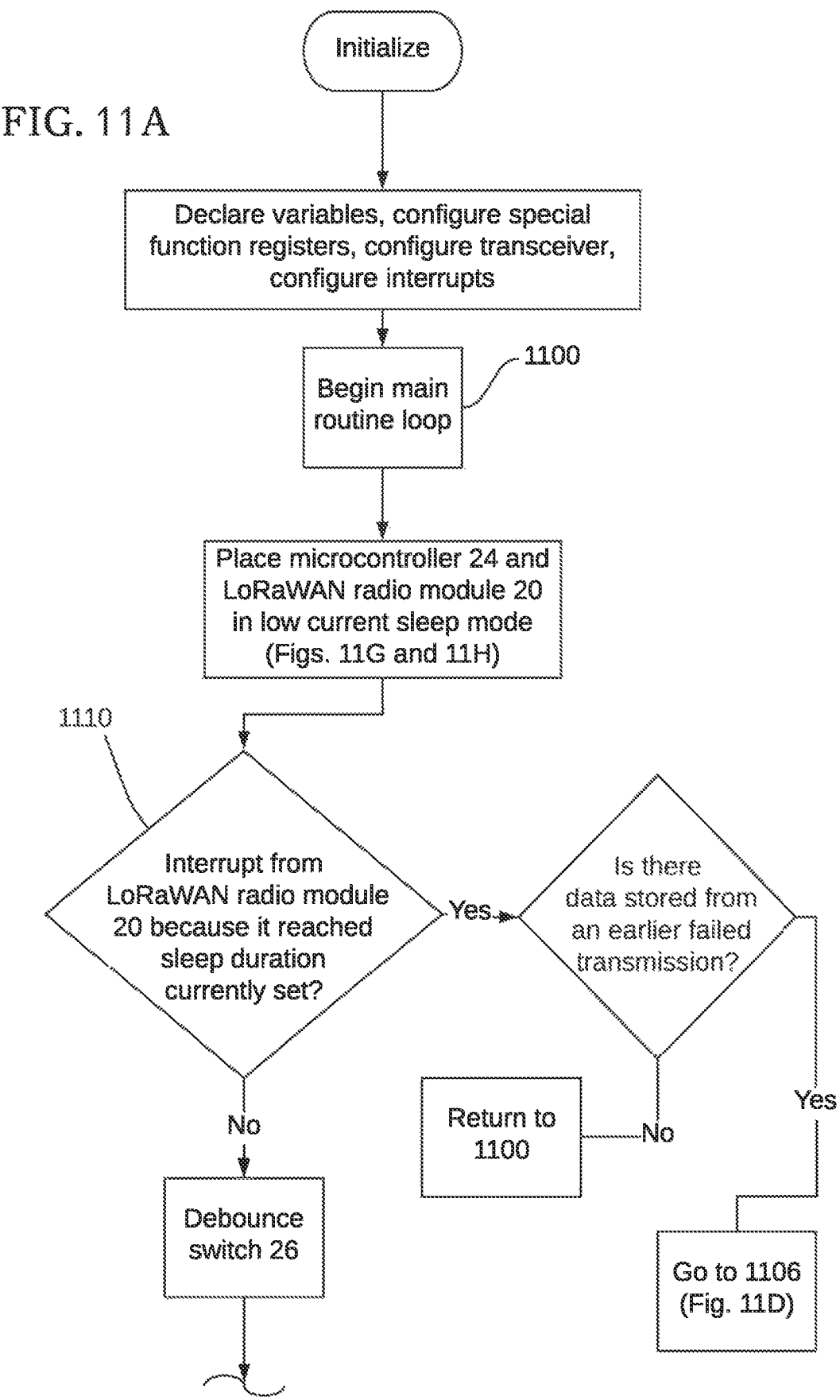
FIGS. 11A-11I show a flowchart for a controller for an embodiment of the present invention.
Figure 11B:
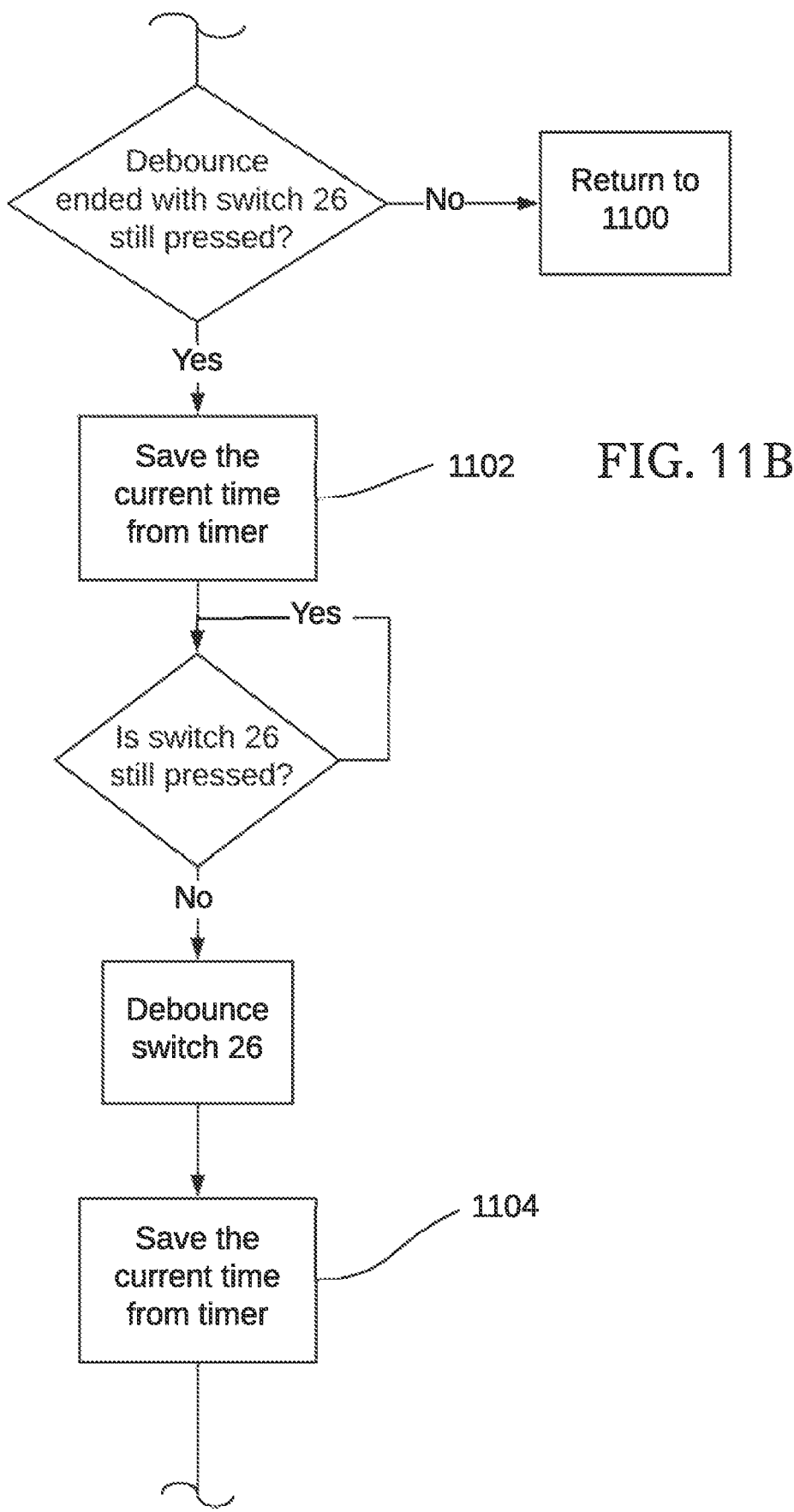
Figure 11C:
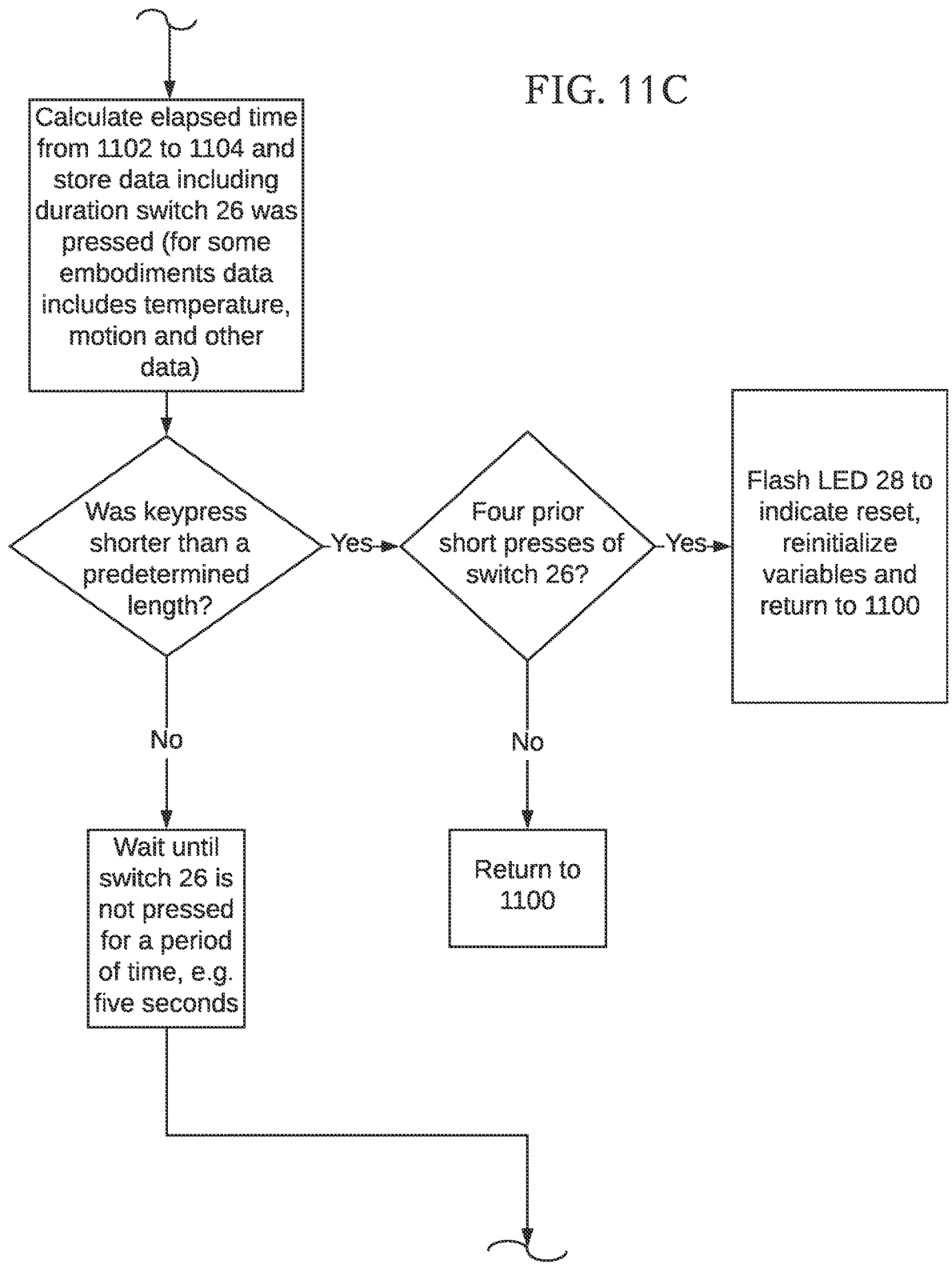
Figure 11D:
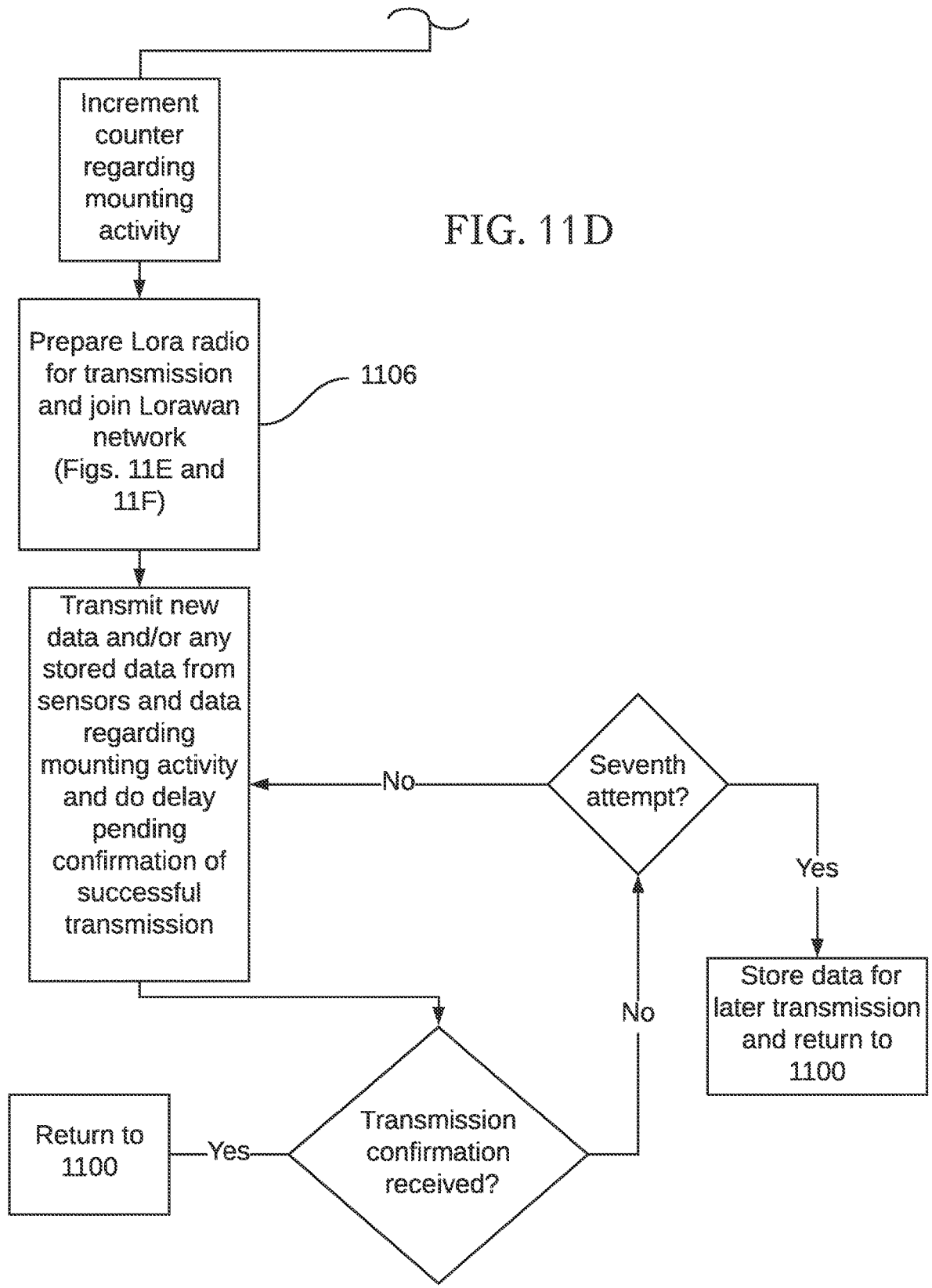
Figure 11E:
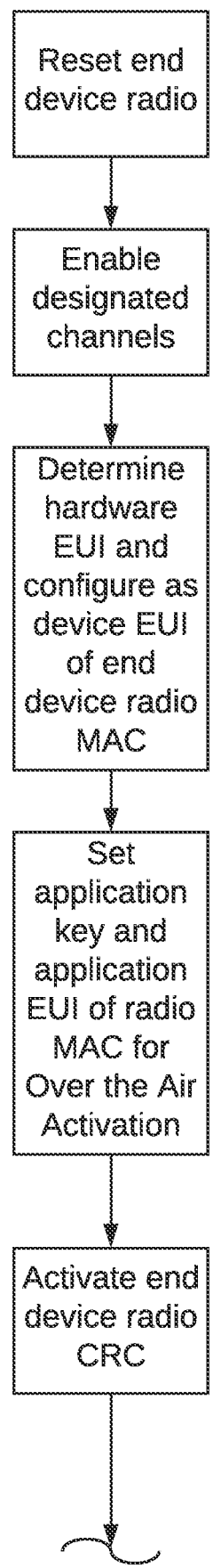
Figure 11F:
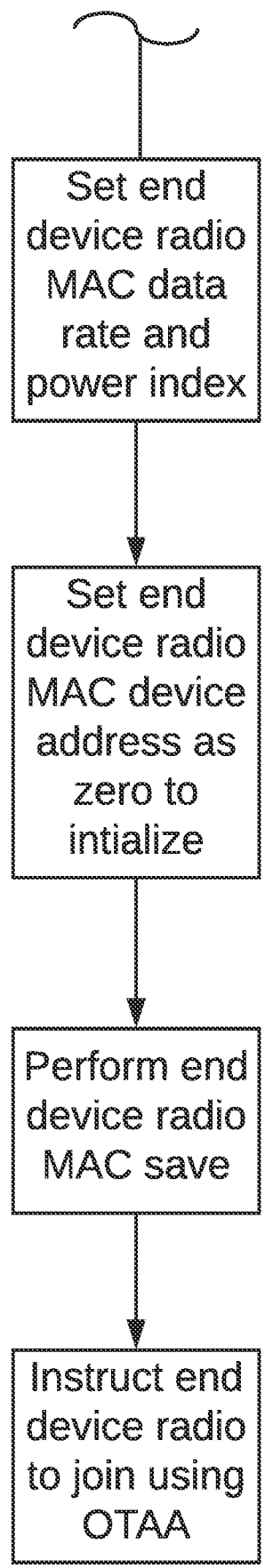
Figure 11G:
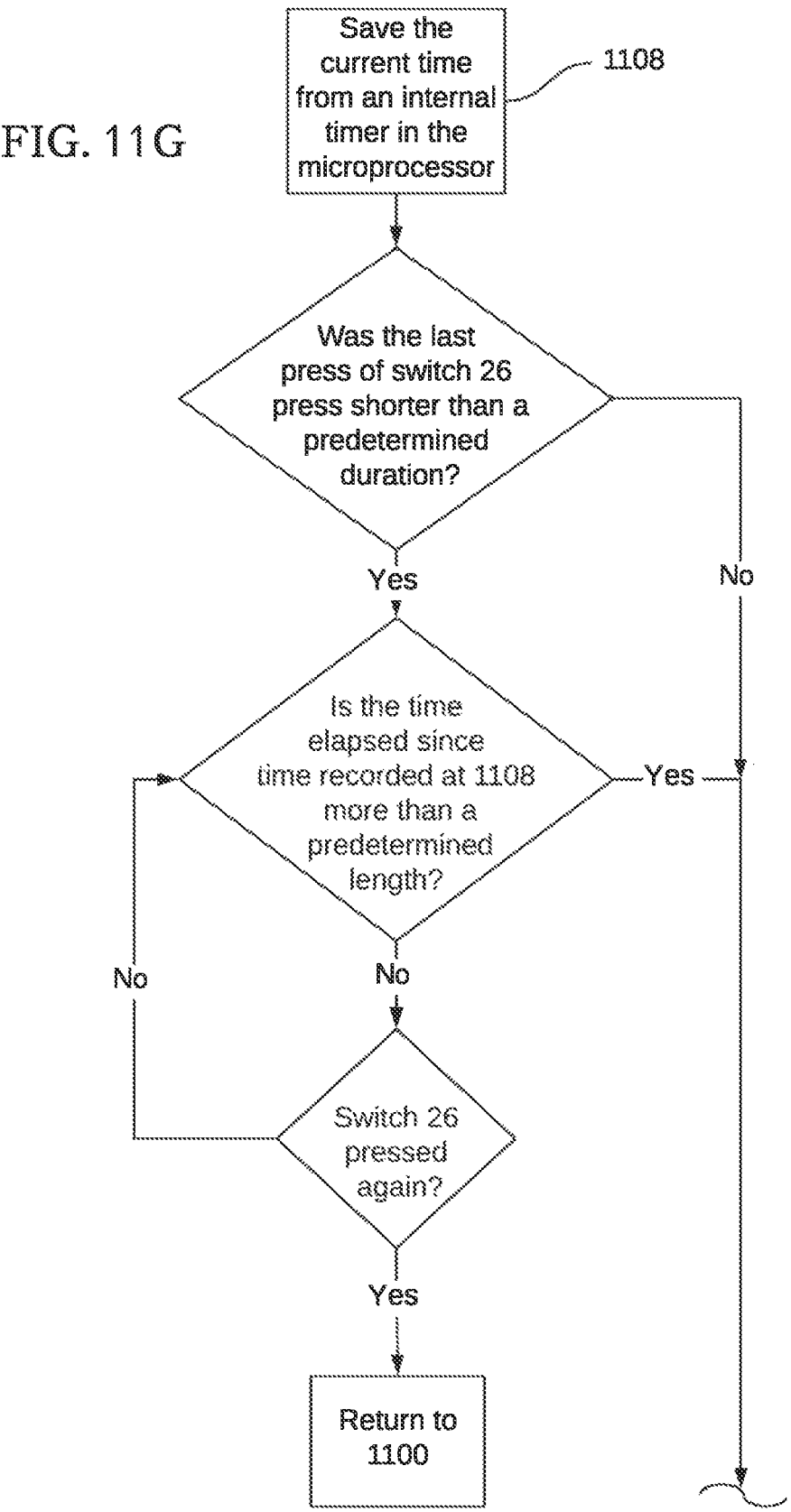
Figure 11H:
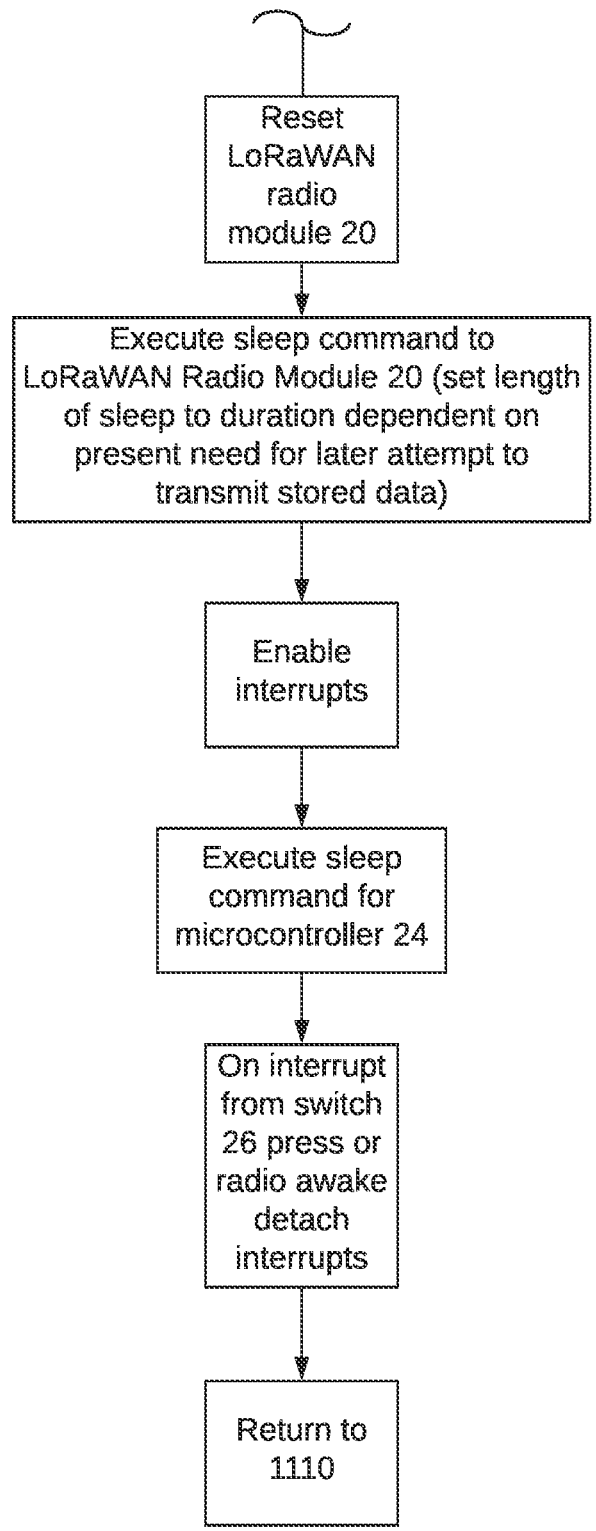
Figure 11I:
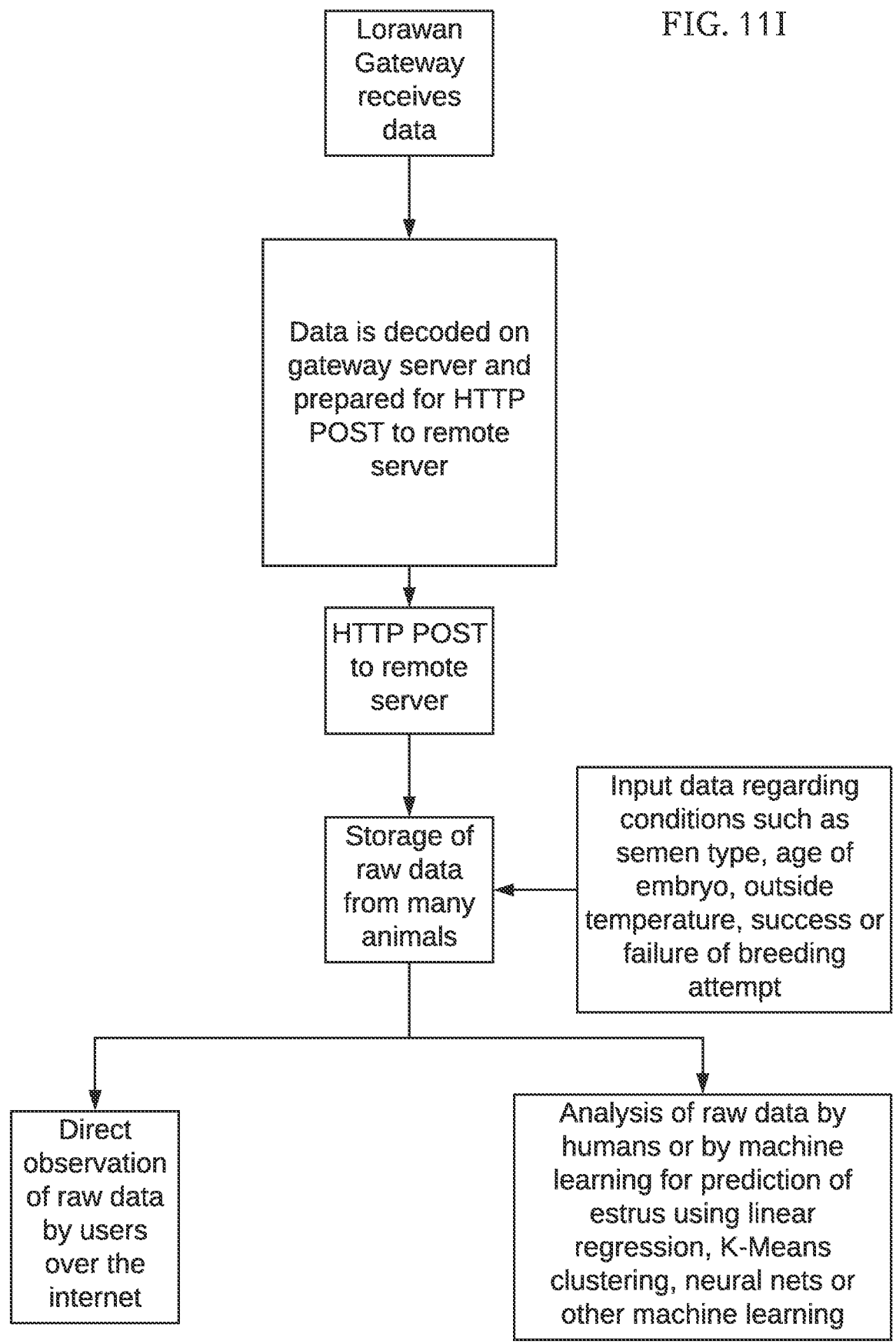

FIGS. 11A-11I show a flowchart for a controller for one embodiment of the present invention. Following the configuration of microcontroller 24, LoRaWAN radio module 20 and microcontroller 24 are placed in low current sleep mode (FIG. 11G and FIG. 11H). The device can be awakened either by a press of switch 26 or by the awakening of the LoRaWAN radio module 20 from a predetermined length of low current sleep mode. The period of sleep for the LoRaWAN radio module 20 can be set for a very lengthy period to conserve power or for shorter periods to attempt retransmission if a transmission fails, as will be described below.

Once an interrupt occurs, if it is an interrupt from the awakening of LoRaWAN radio module 20, LoRaWAN radio module 20 is configured for transmission (FIG. 11E and FIG. 11F), any stored data is transmitted, and LoRaWAN radio module 20 and microcontroller 24 are returned to low current sleep mode (FIG. 11G and FIG. 11H). If the interrupt is the result of a press of switch 26, the time and length of time of the press is measured.

If the press is less than a predetermined length of time, LoRaWAN radio module 20 and microcontroller 24 are returned to low current sleep mode (FIG. 11G and FIG. 11H), unless the press is the fifth consecutive press that is less than a predetermined length of time. In that event, the end device 1 is reset to an initial condition and the recorded number of standing mounts is returned to zero. The use of these five shorter presses as a signal to reset is important so that a key press caused by random activity or animal 52 activity does not cause a reset. If some shorter presses occur but five total presses do not occur within a specified period of time, the device does not reset, LoRaWAN radio module 20 and microcontroller 24 are returned to low current sleep mode (FIG. 11G and FIG. 11H).

If switch 26 is pressed for period greater than a predetermined length of time indicating a standing mount is possible, the end device 1 waits until a 5 second period has occurred in which there was no further presses of switch 26. This is important so that further animal 52 movement or shifting does not result in multiple recorded standing mounts when only one occurred.

LoRaWAN radio module 20 is then configured for transmission (FIG. 11E and FIG. 11F), the number of standing mounts recorded is incremented and that number as well as raw data regarding the actual time and length of time switch 26 was pressed is transmitted. In one embodiment, additional raw data transmitted includes temperature, GPS data, and motion data for a period before the standing mount occurred. If a transmission is not successful after a seventh attempt, the data is stored for later transmission. LoRaWAN radio module 20 and microcontroller 24 are then configured to wake after a period suitable for another transmission attempt and are returned to low current sleep mode (FIG. 11G and FIG. 11H). This is useful, for example, if the animal 52 has temporarily moved to a location that is too distant or transmission is otherwise not possible. If the transmission is successful, LoRaWAN radio module 20 and microcontroller 24 are returned to low current sleep mode (FIG. 11G and FIG. 11H) for a long period of time to conserve energy, unless awakened by a press of switch 26. It must be emphasized that the predetermined length of time required for a press of switch 26 to cause an initial indication of a standing mount is not intended to be used independent of a user determination of the existence of estrus that takes into account the raw data received, including the duration of the mount. As will be discussed more fully below, the present invention permits the user to make determinations based on raw data taking into consideration a variety of factors such as geographic location, motion and restlessness, temperature of the end device 1, temperature of the external environment, type of semen used, age and type of embryo, breed, feeding and nutritional status of the animal 52, and outcome of the breeding effort. This list of factors is only exemplary.

Operation

The end device 1 is first reset by five short presses on button housing 31 to assure that it has been returned to an initial state. If it has not been paired with an identifier linking the end device 1 to a specific animal 52, the user enters into the database the unique identifier of the end device 1 and the user's selected identifier for the animal 52. (FIG. 1B, 146). The database 146 and visual display and means to view and enter data 148 are configured to link the data so that data received in the future from the end device 1 is linked to the user's selected identifier for the animal 52. Said linking process can be modified at any time to permit attachment of the end device 1 to a different animal 52.

The end device 1 is placed into pouch 46 as shown in FIG. 9. Adhesion of the end device 1 to the body of the animal 52 is accomplished by first combing the tailhead of the animal 52 with a curry comb to remove debris and loose hair. A thin layer of adhesive is then applied to the bottom of patch 48 (FIG. 8.) Patch 48 is placed on the area of the tailhead of the animal 52 with end device 1 on the tailhead and with button housing 31 nearest to the tail end of the animal 52 (FIG. 10). The end device 1 is then ready to detect standing mounts and other animal 52 activity and conditions. The details of the operation of the device in response to presses of button housing 31 have been described above. If a transmission occurs, the transmission is received by the LoRaWAN transceiver, gateway and server 140. The data is transferred from the gateway through transmission means 54, which may be wired as shown in FIG. 10 or, in some embodiments, wirelessly. The data is then passed through internet router 142 and remote server 144 to database 146. The data from the transmission is viewable by the user through any media able to view data in the cloud such as cell phones, tablets or other computer devices. The user is also able to enter additional data in database 146 regarding conditions related to the animal 52 associated with the end device 1, including temperature of the external environment, geographic location, type of semen used, age and type of embryo used, feeding and nutritional status of the animal 52, any other data deemed suitable for comparisons with results of attempted insemination or embryo transfer in terms of successful or unsuccessful impregnation and outcome data. Database 146 is designed to accumulate large amounts of data from many users. The accumulation of this raw data and a large number of samples that are compared with success or failure feedback permits the use of analytic tools designed to detect patterns and provide better models for prediction of estrus and better prediction of estrus.

Figure 13:
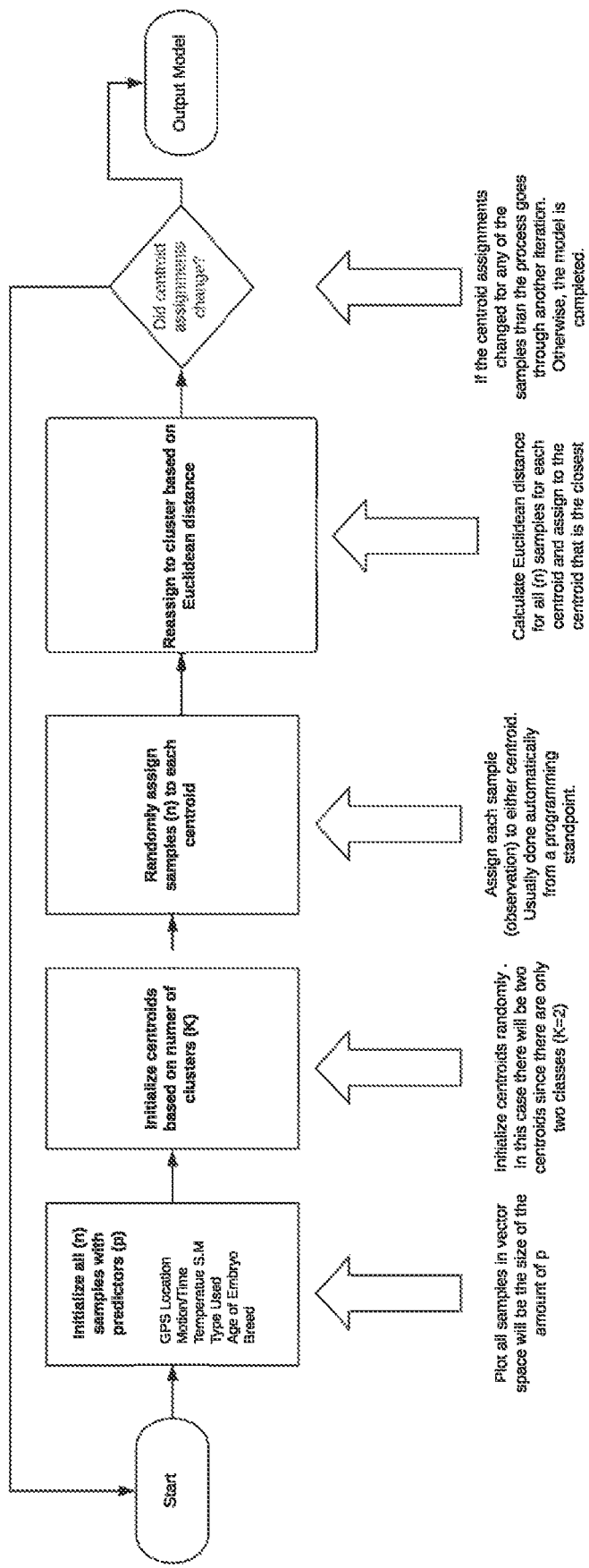
FIG. 13 shows an aspect of an embodiment of the present invention using K-means clustering to determine whether the animal is in estrus.
Figure 14:
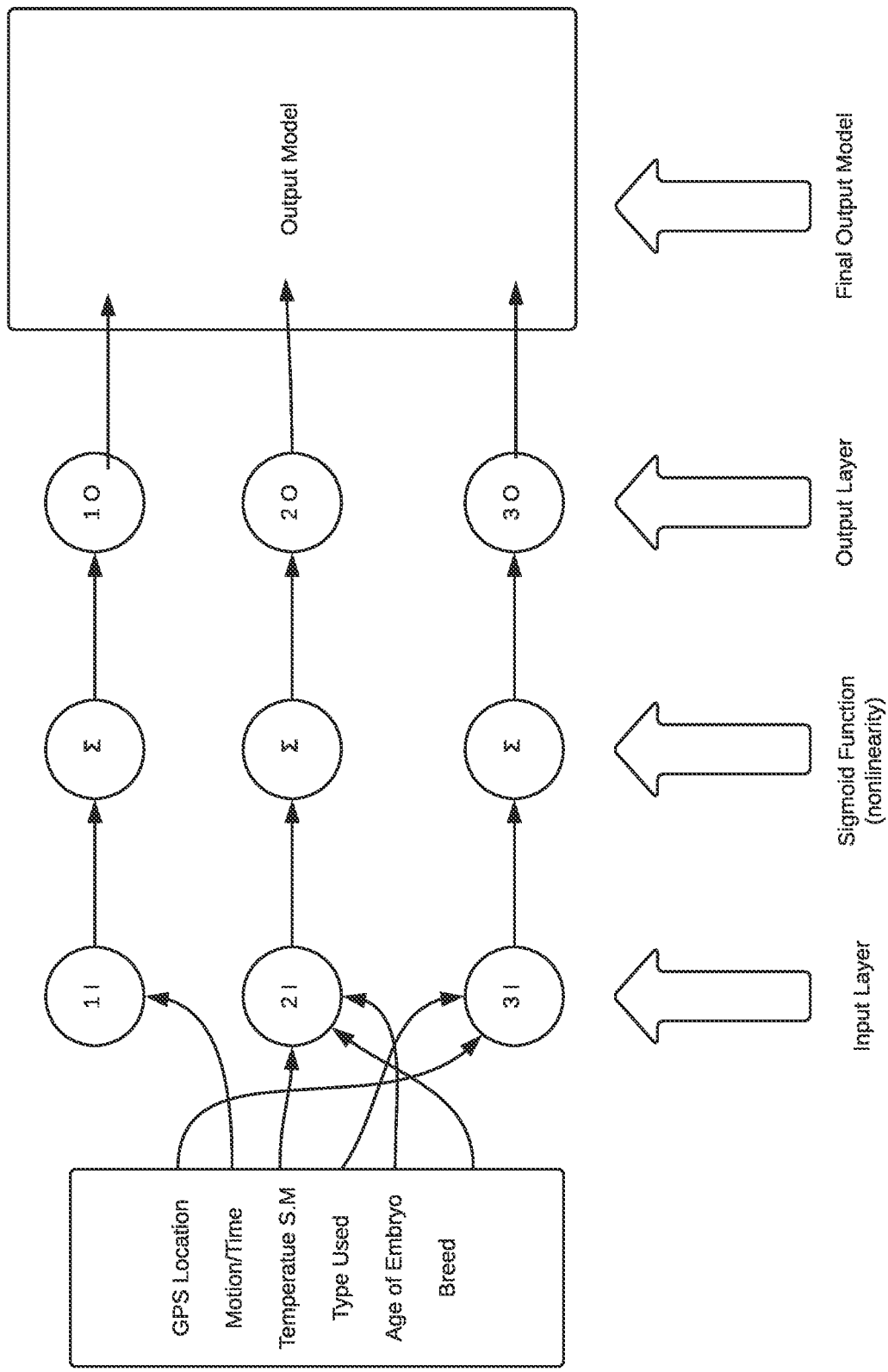
FIG. 14 shows an aspect of an embodiment of the present invention using neural nets to determine whether the animal is in estrus.

For purposes of machine learning, the present invention uses dimensions not requiring the transmission of large amounts of data per transmission. For example, the data regarding motion and restlessness of the animal 52 prior to a standing mount is transmitted as a scalar within a certain range. This permits the transmission of the data through the LoRaWAN protocol, and permits the use of various classification methods to predict estrus. An embodiment of the present invention uses a random forest committee of logistic regression to identify the probability of whether the animal 52 is in estrus. (FIG. 12) Other embodiments of this invention use K-means clustering to determine whether the animal 52 is in estrus. (FIG. 13) Where sufficient dimensions and amount of data exist, other embodiments of this invention use neural nets to determine whether the animal 52 is in estrus. (FIG. 14).

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An apparatus for detecting and reporting breeding behavior of an animal comprising:
   a housing configured to be attached to the animal;
   a circuit board disposed within the housing;
   a battery electronically connected to the circuit board and configured to provide power to the apparatus;
   a switch electronically connected to the circuit board wherein the switch is actuated when a breeding behavior occurs;
   a controller electronically connected to the circuit board, wherein the controller is configured to generate data indicative of breeding behavior upon detecting actuation of the switch;
   a transmitter electronically connected to the circuit board, wherein the transmitter is configured to send dimensions of the data indicative of breeding behavior within a specified range to a remote receiver, wherein the remote receiver is configured to develop a model for predicting estrus in the animal and to update the model periodically based on data received from one or more additional apparatus monitoring breeding behavior of one or more additional animals;
   and a receiver electronically connected to the circuit board, wherein the receiver is configured to receive the updated model from the remote receiver.

2. The apparatus of claim 1 wherein the transmitter comprises a LoRa radio.

3. The apparatus of claim 1 wherein the data sent by the transmitter comprises raw data indicating one or more of a time when breeding behavior occurred, a duration of standing mounts, an ambient temperature, a location of the animal, and history of the animal's motion.

4. The apparatus of claim 1 further comprising a memory electronically connected to the circuit board and configured to store data generated by the apparatus.

5. The apparatus of claim 1 wherein the battery is configured to deliver at least 100 mA of peak current on a repeated basis.

6. The apparatus of claim 5 wherein the battery comprises a coin cell battery with a 300 mAh rating.

7. The apparatus of claim 1 further comprising an antenna electronically connected to the transmitter wherein the antenna is configured to boost a signal transmitted by the transmitter.

8. The apparatus of claim 1 wherein the housing comprises an arched design.

9. The apparatus of claim 1 wherein the circuit board further comprises a silicon coating wherein the silicon coating completely covers the circuit board and one or more components attached to the circuit board.

10. The apparatus of claim 1 further comprising a GPS receiver electronically connected to the circuit board wherein the GPS receiver is configured to receive a signal indicative of the location of the animal.

11. A method for detecting and reporting breeding behavior of an animal comprising:
    providing an apparatus for monitoring breeding behavior of the animal wherein the apparatus is adhered to a tail head of the animal and wherein the apparatus comprises a switch configured to actuate when breeding behavior occurs;
    transmitting dimensions of the data indicative of breeding behavior within a specified range to a remote receiver;
    developing a model at the remote receiver to predict estrus in the animal based on the transmitted data and additional data;
    transferring the model to the apparatus;
    predicting estrus in the animal using the model running on the apparatus;
    updating the model at the remote receiver based on data received from one or more additional apparatus monitoring breeding behavior of one or more additional animals; and
    transferring the updated model to the apparatus.

12. The method of claim 11 further comprising storing data indicative of breeding behavior in a storage device of the apparatus after a failed transmission attempt.

13. The method of claim 12 further comprising retransmitting data to the remote receiver.

14. The method of claim 11 wherein the data indicative of breeding behavior comprises a number of actuations of the switch greater than a predetermined length of time.

15. The method of claim 14 further comprising temporarily blocking transmission of the number of actuations of the switch greater than the predetermined length of time until a second length of time has occurred following a release of the switch in which there were no further presses of the switch.

16. The method of claim 15 wherein the second length of time is five seconds.

17. The method of claim 14 wherein the data indicative of breeding behavior further comprises data regarding the restlessness of the animal.

18. The method of claim 11 wherein transmitting data indicative of breeding behavior to a remote receiver comprises transmission using a LoRaWAN protocol.

19. The method of claim 11 further comprising analyzing the data with a machine learning algorithm to develop a model for the prediction of estrus in animals.

20. A method for detecting and reporting breeding behavior of an animal comprising:
- providing an apparatus for monitoring breeding behavior of the animal wherein the apparatus is adhered to a tail head of the animal and wherein the apparatus comprises a switch configured to actuate when breeding behavior occurs;
- transmitting dimensions of the data indicative of breeding behavior within a specified range to a remote receiver;
- developing a model at the remote receiver to predict estrus in the animal based on the transmitted data and additional data;
- transferring the model to an onboard neural network running on the apparatus and configured to predict estrus in the animal;
- updating the model at the remote receiver based on data received from one or more additional apparatus monitoring breeding behavior of one or more additional animals; and
- transferring the updated model to the onboard neural network running on the apparatus.

* * * * *